(12) United States Patent
Schnittger

(10) Patent No.: US 7,417,179 B1
(45) Date of Patent: Aug. 26, 2008

(54) METHOD OF MODIFYING EPIDERMAL OUTGROWTH STRUCTURES VIA MODULATING CELL CYCLE CONTROL GENES

(75) Inventor: Arp Schnittger, Cologne (DE)

(73) Assignee: CropDesign N.V., Ghent (BE)

( * ) Notice: Subject to any disclaimer, the term of this patent is extended or adjusted under 35 U.S.C. 154(b) by 337 days.

(21) Appl. No.: 10/441,668

(22) Filed: May 19, 2003

Related U.S. Application Data

(60) Provisional application No. 60/381,510, filed on May 17, 2002.

(51) Int. Cl.
*C12N 15/82* (2006.01)
*A01H 5/00* (2006.01)

(52) U.S. Cl. .................... 800/290; 800/287; 800/298; 435/468

(58) Field of Classification Search .................. 800/287, 800/290
See application file for complete search history.

(56) References Cited

U.S. PATENT DOCUMENTS

| | | | | |
|---|---|---|---|---|
| 6,344,601 B1 * | 2/2002 | Chua et al. | ................... | 800/290 |
| 6,559,358 B1 * | 5/2003 | Murray | ....................... | 800/290 |

OTHER PUBLICATIONS

Schnittger A. et al. Ectopic D-type cyclin expression induces not only DNA replication but also cell division in *Arabidopsis* trichomes. Proc Natl Acad Sci U S A. Apr. 30, 2002;99(9):6410-5.*
Sunilkumar G. et al. Developmental and tissue-specific expression on CaMV 35S promoter in cotton as revealed by GFP. Plant Mol Biol. Oct. 2002;50(3):463-74.*
Riou-Khamlichi C. et al. Cytokinin activation of *Arabidopsis* cell division through a D-type cyclin. Science. Mar. 5, 1999;283(5407):1541-4.*
Cockcroft C.E. et al. Cyclin D control of growth rate in plants. Nature. Jun. 1, 2000;405(6786):575-9.*
Renaudin J.P. et al. Plant cyclins: a unified nomenclature for plant A-, B- and D-type cyclins based on sequence organization. Plant Mol Biol. Dec. 1996;32(6):1003-18.*
Cockcroft, C.E. et al. (2000) "Cyclin D control of growth rate in plants", *Nature* 405:575-579.

Day, I.S. et al. (1996) "Isolation of a new mitotic-like cyclin from *Arabidopsis*: complementation of a yeast cyclin mutant with a plant cyclin" *Plant Mol. Biol.*, 30:565-575.
De Veylder, L. et al. (2001) "Functional analysis of cyclin-dependent kinase inhibitors of *Arabidopsis*" *Plant Cell*, 13:1653-1668.
Dixit, R. et al. (2001) "The Brassica MIP-MOD gene encodes a functional water channel that is expressed in the stigma epidermis" *Plant Mol. Biol.*, 45:51-62.
Ivashikina, N. et al. (2001) "K(+) channel profile and electrical properties of *Arabidopsis* root hairs" *FEBS Lett.*, 508:463-469.
Liu, H.C. et al. (2000) "Cloning a promoter analysis of the cotton lipid transfer protein gene Ltp. 3" *Biochem. Biophys. Acta*, 1487:106-111.
Lukowitz, W. et al. (1996) "Cytokinesis in the *Arabidopsis* Embryo Involves the Syntaxin-Related Knolle Gene Product", *Cell*, 84:61-71.
Mandaci, S. et al. (1997) "A promoter directing epidermal expression in transgenic alfalfa" *Plant Mol Biol.*, 34:961-965.
Pichon, M. et al. (1992) "*Rhizobium meliloti* elicits transient expression of the early nodulin gene ENOD12 in the differentiating root epidermis of transgenic alfalfa" *Plant Cell*, 4:1199-1211.
Pyee, J. et al. (1995) "The gene for the major cuticular wax-associated protein and three homologous genes from broccoli (*Brassica oleracea*) and their expression patterns" *Plant J.* 7:49-59.
Riou-Khamlichi, C. et al. (1999) "Cytokinin activation of *Arabidopsis* cell division through a D-type cyclin" *Science* 283 1541-1544.
Schnittger, A. et al. (1998) "Tissue layer and organ specificity of trichome formation are regulated by GLABRA1 and Triptychon in *Arabidopsis*" *Development*, 125:2283-2289.
Szymanski, D.B. et al. (1998) "Control of GL2 expression in *Arabidopsis* leaves and trichomes" *Development*, 125:1161-1171.

* cited by examiner

*Primary Examiner*—Cynthia Collins
(74) *Attorney, Agent, or Firm*—Dilworth & Barrese; Ann R. Pokalsky

(57) ABSTRACT

The present invention provides a method for producing a plant having a modified epidermal outgrowth structure such as a trichome or root hair. The method comprises transforming a plant or plant cell with a D-type cyclin gene operably linked to an epidermis-preferred promoter and regenerating a plant from the transformed plant or plant cell. Examples of epidermis-preferred promoters useful for practicing the present invention include for example, a. lipid transfer protein 3 gene promoter such as an LTP3 promoter, a GLABRA2 gene promoter such as a GL2 promoter, a GORK gene promoter, a MIP-MOD gene promoter, a BLEC4 gene promoter, a WAXD9 gene promoter, and a MtENOD12 gene promoter. Resultant plants having modified epidermal outgrowth structures are also provided.

9 Claims, 10 Drawing Sheets

SEQUENCE LISTING

```
<160> NUMBER OF SEQ ID NOS: 11

<210> SEQ ID NO 1
<211> LENGTH: 1131
<212> TYPE: DNA
<213> ORGANISM: Arabidopsis thaliana
<220> FEATURE:
<221> NAME/KEY: CDS
<222> LOCATION: (1)..(1131)

<400> SEQUENCE: 1
```

-continued

| | | |
|---|---|---|
| atg gcg att cgg aag gag gaa gaa agt aga gaa gaa cag agc aat tcg<br>Met Ala Ile Arg Lys Glu Glu Glu Ser Arg Glu Glu Gln Ser Asn Ser<br>1                  5                    10                15 | | 48 |
| ttt ctt ctt gat gct ctc tac tgc gaa gaa gag aaa tgg gac gat gaa<br>Phe Leu Leu Asp Ala Leu Tyr Cys Glu Glu Glu Lys Trp Asp Asp Glu<br>                  20                    25                    30 | | 96 |
| gga gaa gaa gtt gaa gaa aac tct tcc ttg tct tct tct tct tct cca<br>Gly Glu Glu Val Glu Glu Asn Ser Ser Leu Ser Ser Ser Ser Ser Pro<br>        35                    40                    45 | | 144 |
| ttc gtt gtt ttg caa caa gat ttg ttc tgg gaa gat gaa gat ctg gtt<br>Phe Val Val Leu Gln Gln Asp Leu Phe Trp Glu Asp Glu Asp Leu Val<br>50                      55                    60 | | 192 |
| aca ctc ttc tcc aaa gaa gaa gaa caa gga ctc agc tgt ctc gat gat<br>Thr Leu Phe Ser Lys Glu Glu Glu Gln Gly Leu Ser Cys Leu Asp Asp<br>65                      70                    75                80 | | 240 |
| gtt tat ctt tcc acg gat cga aaa gaa gct gtt ggt tgg att ctg aga<br>Val Tyr Leu Ser Thr Asp Arg Lys Glu Ala Val Gly Trp Ile Leu Arg<br>                  85                    90                    95 | | 288 |
| gtc aac gct cat tat ggc ttc tct act tta gca gct gtt tta gcc ata<br>Val Asn Ala His Tyr Gly Phe Ser Thr Leu Ala Ala Val Leu Ala Ile<br>                    100                    105                110 | | 336 |
| act tat ctc gat aag ttc atc tgt agc tac agc tta cag aga gac aaa<br>Thr Tyr Leu Asp Lys Phe Ile Cys Ser Tyr Ser Leu Gln Arg Asp Lys<br>                115                    120                    125 | | 384 |
| cca tgg atg ctt cag ctc gtt tct gtc gcg tgt ctc tca tta gct gct<br>Pro Trp Met Leu Gln Leu Val Ser Val Ala Cys Leu Ser Leu Ala Ala<br>130                      135                    140 | | 432 |
| aaa gtc gaa gaa acc caa gtc cct ctt ctt cta gac ttt caa gtg gag<br>Lys Val Glu Glu Thr Gln Val Pro Leu Leu Leu Asp Phe Gln Val Glu<br>145                      150                    155                160 | | 480 |
| gag aca aag tat gtg ttt gaa gca aaa acc ata cag aga atg gag cta<br>Glu Thr Lys Tyr Val Phe Glu Ala Lys Thr Ile Gln Arg Met Glu Leu<br>                    165                    170                    175 | | 528 |
| ctg att ctg tct act ctc gag tgg aag atg cat ctc att act cca att<br>Leu Ile Leu Ser Thr Leu Glu Trp Lys Met His Leu Ile Thr Pro Ile<br>                180                    185                    190 | | 576 |
| tcg ttc gta gac cac att atc agg aga ttg gga ctt aag aac aat gct<br>Ser Phe Val Asp His Ile Ile Arg Arg Leu Gly Leu Lys Asn Asn Ala<br>                    195                    200                    205 | | 624 |
| cac tgg gat ttc ctc aac aaa tgc cac cgt ctc ctc ctc tct gta atc<br>His Trp Asp Phe Leu Asn Lys Cys His Arg Leu Leu Leu Ser Val Ile<br>              210                    215                    220 | | 672 |
| tcc gat tca aga ttt gtc ggg tac ctc cca tca gta gtt gcc gca gct<br>Ser Asp Ser Arg Phe Val Gly Tyr Leu Pro Ser Val Val Ala Ala Ala<br>225                      230                    235                240 | | 720 |
| acc atg atg cga att ata gag caa gtt gat ccc ttt gac cct ctt tca<br>Thr Met Met Arg Ile Ile Glu Gln Val Asp Pro Phe Asp Pro Leu Ser<br>                    245                    250                    255 | | 768 |
| tac caa act aat ctc ctc ggt gtc ctt aac tta acc aag gaa aag gtg<br>Tyr Gln Thr Asn Leu Leu Gly Val Leu Asn Leu Thr Lys Glu Lys Val<br>                260                    265                    270 | | 816 |
| aaa act tgc tac gat cta atc ctc caa cta cca gtg gac cgc atc ggt<br>Lys Thr Cys Tyr Asp Leu Ile Leu Gln Leu Pro Val Asp Arg Ile Gly<br>              275                    280                    285 | | 864 |
| tta cag atc caa atc caa tct tcc aag aaa cgc aag agt cac gat tca<br>Leu Gln Ile Gln Ile Gln Ser Ser Lys Lys Arg Lys Ser His Asp Ser<br>              290                    295                    300 | | 912 |
| tca tca tcg ttg aac agt cca agc tgc gtg att gat gca aac cct ttc<br>Ser Ser Ser Leu Asn Ser Pro Ser Cys Val Ile Asp Ala Asn Pro Phe | | 960 |

-continued

```
                305                 310                 315                 320
aat agc gac gaa agc tca aac gat tcg tgg tca gcg agt tcg tgc aac       1008
Asn Ser Asp Glu Ser Ser Asn Asp Ser Trp Ser Ala Ser Ser Cys Asn
                325                 330                 335 cca cca acg tcg tcg tcc ccg cag caa caa cct cca ttg aag aag           1056
Pro Pro Thr Ser Ser Ser Pro Gln Gln Gln Pro Pro Leu Lys Lys
            340                 345                 350 atg aga gga gct gaa gag aat gag aag aag aag ccg att ttg cat ctg       1104
Met Arg Gly Ala Glu Glu Asn Glu Lys Lys Lys Pro Ile Leu His Leu
        355                 360                 365 cca tgg gca atc gta gcc act cca taa                                   1131
Pro Trp Ala Ile Val Ala Thr Pro
        370                 375
```

<210> SEQ ID NO 2
<211> LENGTH: 376
<212> TYPE: PRT
<213> ORGANISM: Arabidopsis thaliana

<400> SEQUENCE: 2

```
Met Ala Ile Arg Lys Glu Glu Ser Arg Glu Glu Gln Ser Asn Ser
1               5                   10                  15

Phe Leu Leu Asp Ala Leu Tyr Cys Glu Glu Lys Trp Asp Asp Glu
                20                  25                  30

Gly Glu Glu Val Glu Glu Asn Ser Ser Leu Ser Ser Ser Ser Pro
            35                  40                  45

Phe Val Val Leu Gln Gln Asp Leu Phe Trp Glu Asp Glu Asp Leu Val
        50                  55                  60

Thr Leu Phe Ser Lys Glu Glu Glu Gln Gly Leu Ser Cys Leu Asp Asp
65                  70                  75                  80

Val Tyr Leu Ser Thr Asp Arg Lys Glu Ala Val Gly Trp Ile Leu Arg
                85                  90                  95

Val Asn Ala His Tyr Gly Phe Ser Thr Leu Ala Ala Val Leu Ala Ile
                100                 105                 110

Thr Tyr Leu Asp Lys Phe Ile Cys Ser Tyr Ser Leu Gln Arg Asp Lys
            115                 120                 125

Pro Trp Met Leu Gln Leu Val Ser Val Ala Cys Leu Ser Leu Ala Ala
        130                 135                 140

Lys Val Glu Glu Thr Gln Val Pro Leu Leu Leu Asp Phe Gln Val Glu
145                 150                 155                 160

Glu Thr Lys Tyr Val Phe Glu Ala Lys Thr Ile Gln Arg Met Glu Leu
                165                 170                 175

Leu Ile Leu Ser Thr Leu Glu Trp Lys Met His Leu Ile Thr Pro Ile
            180                 185                 190

Ser Phe Val Asp His Ile Ile Arg Arg Leu Gly Leu Lys Asn Asn Ala
        195                 200                 205

His Trp Asp Phe Leu Asn Lys Cys His Arg Leu Leu Ser Val Ile
    210                 215                 220

Ser Asp Ser Arg Phe Val Gly Tyr Leu Pro Ser Val Ala Ala Ala
225                 230                 235                 240

Thr Met Met Arg Ile Ile Glu Gln Val Asp Pro Phe Asp Pro Leu Ser
                245                 250                 255

Tyr Gln Thr Asn Leu Leu Gly Val Leu Asn Leu Thr Lys Glu Lys Val
            260                 265                 270

Lys Thr Cys Tyr Asp Leu Ile Leu Gln Leu Pro Val Asp Arg Ile Gly
        275                 280                 285
```

-continued

```
Leu Gln Ile Gln Ile Gln Ser Ser Lys Lys Arg Lys Ser His Asp Ser
    290                 295                 300
Ser Ser Ser Leu Asn Ser Pro Ser Cys Val Ile Asp Ala Asn Pro Phe
305                 310                 315                 320
Asn Ser Asp Glu Ser Ser Asn Asp Ser Trp Ser Ala Ser Ser Cys Asn
                325                 330                 335
Pro Pro Thr Ser Ser Ser Pro Gln Gln Gln Pro Pro Leu Lys Lys
            340                 345                 350
Met Arg Gly Ala Glu Glu Asn Glu Lys Lys Lys Pro Ile Leu His Leu
        355                 360                 365
Pro Trp Ala Ile Val Ala Thr Pro
    370                 375

<210> SEQ ID NO 3
<211> LENGTH: 1338
<212> TYPE: DNA
<213> ORGANISM: Arabidopsis thaliana
<220> FEATURE:
<221> NAME/KEY: CDS
<222> LOCATION: (1)..(1338)

<400> SEQUENCE: 3
```

| | | | | | | | | | | | | | | | | |
|---|---|---|---|---|---|---|---|---|---|---|---|---|---|---|---|---|
| atg gcg acg aga gca aac gta cct gaa caa gtc aga ggt gct cct ctc | | | | | | | | | | | | | | | | 48 |
| Met Ala Thr Arg Ala Asn Val Pro Glu Gln Val Arg Gly Ala Pro Leu | | | | | | | | | | | | | | | | |
| 1 | | | 5 | | | | | 10 | | | | | 15 | | | |
| gtt gat ggt ttg aag att cag aac aaa aac ggt gct gtg aag agt cgg | | | | | | | | | | | | | | | | 96 |
| Val Asp Gly Leu Lys Ile Gln Asn Lys Asn Gly Ala Val Lys Ser Arg | | | | | | | | | | | | | | | | |
| | | | | 20 | | | | | 25 | | | | | 30 | | |
| cgt gcc ctc ggt gac atc gga aat ctt gtt tct gtt ccc gga gtt caa | | | | | | | | | | | | | | | | 144 |
| Arg Ala Leu Gly Asp Ile Gly Asn Leu Val Ser Val Pro Gly Val Gln | | | | | | | | | | | | | | | | |
| | | 35 | | | | | 40 | | | | | 45 | | | | |
| gga gga aag gct caa cct ccg att aat cga ccc att act cga agt ttc | | | | | | | | | | | | | | | | 192 |
| Gly Gly Lys Ala Gln Pro Pro Ile Asn Arg Pro Ile Thr Arg Ser Phe | | | | | | | | | | | | | | | | |
| 50 | | | | | 55 | | | | | 60 | | | | | | |
| cgt gcc cag tta tta gcg aat gcc caa ctc gaa aga aag cca atc aat | | | | | | | | | | | | | | | | 240 |
| Arg Ala Gln Leu Leu Ala Asn Ala Gln Leu Glu Arg Lys Pro Ile Asn | | | | | | | | | | | | | | | | |
| 65 | | | | | 70 | | | | | 75 | | | | | 80 | |
| gga gac aac aag gtt cca gct ctt ggt cca aag aga caa cct ctt gct | | | | | | | | | | | | | | | | 288 |
| Gly Asp Asn Lys Val Pro Ala Leu Gly Pro Lys Arg Gln Pro Leu Ala | | | | | | | | | | | | | | | | |
| | | | | 85 | | | | | 90 | | | | | 95 | | |
| gca aga aac cca gaa gct caa agg gcg gtt cag aag aag aat cta gtg | | | | | | | | | | | | | | | | 336 |
| Ala Arg Asn Pro Glu Ala Gln Arg Ala Val Gln Lys Lys Asn Leu Val | | | | | | | | | | | | | | | | |
| | | | 100 | | | | | 105 | | | | | 110 | | | |
| gtt aag caa cag acg aag cct gtt gaa gtg atc gag acg aag aag gag | | | | | | | | | | | | | | | | 384 |
| Val Lys Gln Gln Thr Lys Pro Val Glu Val Ile Glu Thr Lys Lys Glu | | | | | | | | | | | | | | | | |
| | | 115 | | | | | 120 | | | | | 125 | | | | |
| gtg act aaa aag gaa gta gcg atg tca cct aag aat aag aaa gtg acg | | | | | | | | | | | | | | | | 432 |
| Val Thr Lys Lys Glu Val Ala Met Ser Pro Lys Asn Lys Lys Val Thr | | | | | | | | | | | | | | | | |
| 130 | | | | | 135 | | | | | 140 | | | | | | |
| tac tcg tct gta ctt agt gct cgg agc aaa gct gct tgt ggt ata gtc | | | | | | | | | | | | | | | | 480 |
| Tyr Ser Ser Val Leu Ser Ala Arg Ser Lys Ala Ala Cys Gly Ile Val | | | | | | | | | | | | | | | | |
| 145 | | | | | 150 | | | | | 155 | | | | | 160 | |
| aac aaa cca aag att atc gat att gat gaa tct gac aaa gat aac cat | | | | | | | | | | | | | | | | 528 |
| Asn Lys Pro Lys Ile Ile Asp Ile Asp Glu Ser Asp Lys Asp Asn His | | | | | | | | | | | | | | | | |
| | | | | 165 | | | | | 170 | | | | | 175 | | |
| ttg gct gcg gtg gag tat gtt gat gat atg tac tcg ttc tat aaa gaa | | | | | | | | | | | | | | | | 576 |
| Leu Ala Ala Val Glu Tyr Val Asp Asp Met Tyr Ser Phe Tyr Lys Glu | | | | | | | | | | | | | | | | |
| | | | 180 | | | | | 185 | | | | | 190 | | | |
| gtt gag aag gag agt cag cct aag atg tac atg cac att cag act gaa | | | | | | | | | | | | | | | | 624 |

```
Val Glu Lys Glu Ser Gln Pro Lys Met Tyr Met His Ile Gln Thr Glu
        195                 200                 205 atg aat gag aag atg aga gcg atc ttg att gat tgg tta cta gaa gtt    672
Met Asn Glu Lys Met Arg Ala Ile Leu Ile Asp Trp Leu Leu Glu Val
    210                 215                 220 cac atc aag ttt gag ctc aac ctt gaa act ctg tac ctc acc gtc aac    720
His Ile Lys Phe Glu Leu Asn Leu Glu Thr Leu Tyr Leu Thr Val Asn
225                 230                 235                 240 atc att gat cga ttc ctc tct gtg aaa gct gtc cct aaa aga gag tta    768
Ile Ile Asp Arg Phe Leu Ser Val Lys Ala Val Pro Lys Arg Glu Leu
                245                 250                 255 cag cta gtg gga atc agt gcc ttg ctt att gct tcc aaa tat gaa gaa    816
Gln Leu Val Gly Ile Ser Ala Leu Leu Ile Ala Ser Lys Tyr Glu Glu
            260                 265                 270 atc tgg cca cct cag gtt aac gat ctg gtg tat gtc acg gac aat gct    864
Ile Trp Pro Pro Gln Val Asn Asp Leu Val Tyr Val Thr Asp Asn Ala
        275                 280                 285 tac agt agc aga cag att ctg gtg atg gag aag gca att ctt gga aac    912
Tyr Ser Ser Arg Gln Ile Leu Val Met Glu Lys Ala Ile Leu Gly Asn
    290                 295                 300 ctc gaa tgg tat ttg aca gtc ccg act caa tac gtc ttc ctt gtc cgc    960
Leu Glu Trp Tyr Leu Thr Val Pro Thr Gln Tyr Val Phe Leu Val Arg
305                 310                 315                 320 ttc atc aaa gct tcg atg tct gat cca gaa atg gag aat atg gtt cac   1008
Phe Ile Lys Ala Ser Met Ser Asp Pro Glu Met Glu Asn Met Val His
                325                 330                 335 ttc ctt gct gaa ttg ggg atg atg cat tac gac acc ttg acg ttc tgt   1056
Phe Leu Ala Glu Leu Gly Met Met His Tyr Asp Thr Leu Thr Phe Cys
            340                 345                 350 ccc tcc atg ctt gct gct tca gct gtt tac acg gca aga tgc tca ttg   1104
Pro Ser Met Leu Ala Ala Ser Ala Val Tyr Thr Ala Arg Cys Ser Leu
        355                 360                 365 aac aag tcc cct gct tgg act gat aca ttg cag ttc cac acc ggc tac   1152
Asn Lys Ser Pro Ala Trp Thr Asp Thr Leu Gln Phe His Thr Gly Tyr
    370                 375                 380 aca gag tct gag att atg gac tgc tca aag ctt tta gct ttt ctt cac   1200
Thr Glu Ser Glu Ile Met Asp Cys Ser Lys Leu Leu Ala Phe Leu His
385                 390                 395                 400 tcg aga tgc ggt gag agc agg cta cgt gca gtg tac aag aag tac tcg   1248
Ser Arg Cys Gly Glu Ser Arg Leu Arg Ala Val Tyr Lys Lys Tyr Ser
                405                 410                 415 aag gca gag aat gga ggt gtt gct atg gtt tct ccg gcc aag tct ctc   1296
Lys Ala Glu Asn Gly Gly Val Ala Met Val Ser Pro Ala Lys Ser Leu
            420                 425                 430 ttg agt gct gct gct gat tgg aag aag cct gtt tct tct tag           1338
Leu Ser Ala Ala Ala Asp Trp Lys Lys Pro Val Ser Ser
        435                 440                 445

<210> SEQ ID NO 4
<211> LENGTH: 445
<212> TYPE: PRT
<213> ORGANISM: Arabidopsis thaliana

<400> SEQUENCE: 4

Met Ala Thr Arg Ala Asn Val Pro Glu Gln Val Arg Gly Ala Pro Leu
1               5                   10                  15

Val Asp Gly Leu Lys Ile Gln Asn Lys Asn Gly Ala Val Lys Ser Arg
            20                  25                  30

Arg Ala Leu Gly Asp Ile Gly Asn Leu Val Ser Val Pro Gly Val Gln
        35                  40                  45
```

```
Gly Gly Lys Ala Gln Pro Pro Ile Asn Arg Pro Ile Thr Arg Ser Phe
 50                  55                  60

Arg Ala Gln Leu Leu Ala Asn Ala Gln Leu Glu Arg Lys Pro Ile Asn
 65                  70                  75                  80

Gly Asp Asn Lys Val Pro Ala Leu Gly Pro Lys Arg Gln Pro Leu Ala
                 85                  90                  95

Ala Arg Asn Pro Glu Ala Gln Arg Ala Val Gln Lys Lys Asn Leu Val
            100                 105                 110

Val Lys Gln Gln Thr Lys Pro Val Glu Val Ile Glu Thr Lys Lys Glu
            115                 120                 125

Val Thr Lys Lys Glu Val Ala Met Ser Pro Lys Asn Lys Lys Val Thr
130                 135                 140

Tyr Ser Ser Val Leu Ser Ala Arg Ser Lys Ala Ala Cys Gly Ile Val
145                 150                 155                 160

Asn Lys Pro Lys Ile Ile Asp Ile Asp Glu Ser Asp Lys Asp Asn His
                165                 170                 175

Leu Ala Ala Val Glu Tyr Val Asp Asp Met Tyr Ser Phe Tyr Lys Glu
            180                 185                 190

Val Glu Lys Glu Ser Gln Pro Lys Met Tyr Met His Ile Gln Thr Glu
            195                 200                 205

Met Asn Glu Lys Met Arg Ala Ile Leu Ile Asp Trp Leu Leu Glu Val
210                 215                 220

His Ile Lys Phe Glu Leu Asn Leu Glu Thr Leu Tyr Leu Thr Val Asn
225                 230                 235                 240

Ile Ile Asp Arg Phe Leu Ser Val Lys Ala Val Pro Lys Arg Glu Leu
                245                 250                 255

Gln Leu Val Gly Ile Ser Ala Leu Leu Ile Ala Ser Lys Tyr Glu Glu
            260                 265                 270

Ile Trp Pro Pro Gln Val Asn Asp Leu Val Tyr Val Thr Asp Asn Ala
            275                 280                 285

Tyr Ser Ser Arg Gln Ile Leu Val Met Glu Lys Ala Ile Leu Gly Asn
290                 295                 300

Leu Glu Trp Tyr Leu Thr Val Pro Thr Gln Tyr Val Phe Leu Val Arg
305                 310                 315                 320

Phe Ile Lys Ala Ser Met Ser Asp Pro Glu Met Glu Asn Met Val His
                325                 330                 335

Phe Leu Ala Glu Leu Gly Met Met His Tyr Asp Thr Leu Thr Phe Cys
            340                 345                 350

Pro Ser Met Leu Ala Ala Ser Ala Val Tyr Thr Ala Arg Cys Ser Leu
            355                 360                 365

Asn Lys Ser Pro Ala Trp Thr Asp Thr Leu Gln Phe His Thr Gly Tyr
370                 375                 380

Thr Glu Ser Glu Ile Met Asp Cys Ser Lys Leu Leu Ala Phe Leu His
385                 390                 395                 400

Ser Arg Cys Gly Glu Ser Arg Leu Arg Ala Val Tyr Lys Lys Tyr Ser
                405                 410                 415

Lys Ala Glu Asn Gly Gly Val Ala Met Val Ser Pro Ala Lys Ser Leu
            420                 425                 430

Leu Ser Ala Ala Ala Asp Trp Lys Lys Pro Val Ser Ser
435                 440                 445
```

<210> SEQ ID NO 5
<211> LENGTH: 576

<210> TYPE: DNA
<213> ORGANISM: Arabidopsis thaliana
<220> FEATURE:
<221> NAME/KEY: CDS
<222> LOCATION: (1)..(576)

<400> SEQUENCE: 5

```
atg gtg aga aaa tat aga aaa gct aaa gga att gta gaa gct gga gtt      48
Met Val Arg Lys Tyr Arg Lys Ala Lys Gly Ile Val Glu Ala Gly Val
1               5                  10                  15 tcg tca acg tat atg cag cta cgg agc cgg aga att gtt tat gtt aga      96
Ser Ser Thr Tyr Met Gln Leu Arg Ser Arg Arg Ile Val Tyr Val Arg
                20                  25                  30 tcg gaa aaa tca agc tct gtc tcc gtc gtc ggt gat aat gga gtt tcg     144
Ser Glu Lys Ser Ser Ser Val Ser Val Val Gly Asp Asn Gly Val Ser
            35                  40                  45 tcg tct tgt agt gga agc aat gaa tat aag aag aaa gaa tta ata cat     192
Ser Ser Cys Ser Gly Ser Asn Glu Tyr Lys Lys Lys Glu Leu Ile His
        50                  55                  60 ctg gag gag gaa gat aaa gat ggt gac act gaa acg tcg acg tat cga     240
Leu Glu Glu Glu Asp Lys Asp Gly Asp Thr Glu Thr Ser Thr Tyr Arg
65                  70                  75                  80 cgg ggt acg aag agg aag ctt ttt gaa aat ctg aga gag gag gag aaa     288
Arg Gly Thr Lys Arg Lys Leu Phe Glu Asn Leu Arg Glu Glu Glu Lys
                85                  90                  95 gaa gaa tta agt aaa tcc atg gag aat tat tca tcg gaa ttt gaa tcg     336
Glu Glu Leu Ser Lys Ser Met Glu Asn Tyr Ser Ser Glu Phe Glu Ser
                100                 105                 110 gcg gtt aaa gaa tcg tta gat tgt tgt tgt agc ggg agg aaa acg atg     384
Ala Val Lys Glu Ser Leu Asp Cys Cys Cys Ser Gly Arg Lys Thr Met
            115                 120                 125 gag gag acg gtg acg gcg gag gag gag gag aag gcg aaa ttg atg acg     432
Glu Glu Thr Val Thr Ala Glu Glu Glu Glu Lys Ala Lys Leu Met Thr
        130                 135                 140 gag atg cca acg gaa tcg gaa att gaa gat ttt ttt gtg gaa gct gag     480
Glu Met Pro Thr Glu Ser Glu Ile Glu Asp Phe Phe Val Glu Ala Glu
145                 150                 155                 160 aaa caa ctc aaa gaa aaa ttc aag aag aag tac aat ttc gat ttc gag     528
Lys Gln Leu Lys Glu Lys Phe Lys Lys Lys Tyr Asn Phe Asp Phe Glu
                165                 170                 175 aag gag aag cca tta gaa gga cgt tac gaa tgg gta aag tta gag tga    576
Lys Glu Lys Pro Leu Glu Gly Arg Tyr Glu Trp Val Lys Leu Glu
                180                 185                 190
```

<210> SEQ ID NO 6
<211> LENGTH: 191
<212> TYPE: PRT
<213> ORGANISM: Arabidopsis thaliana

<400> SEQUENCE: 6

```
Met Val Arg Lys Tyr Arg Lys Ala Lys Gly Ile Val Glu Ala Gly Val
1               5                  10                  15

Ser Ser Thr Tyr Met Gln Leu Arg Ser Arg Arg Ile Val Tyr Val Arg
                20                  25                  30

Ser Glu Lys Ser Ser Ser Val Ser Val Val Gly Asp Asn Gly Val Ser
            35                  40                  45

Ser Ser Cys Ser Gly Ser Asn Glu Tyr Lys Lys Lys Glu Leu Ile His
        50                  55                  60

Leu Glu Glu Glu Asp Lys Asp Gly Asp Thr Glu Thr Ser Thr Tyr Arg
65                  70                  75                  80
```

```
Arg Gly Thr Lys Arg Lys Leu Phe Glu Asn Leu Arg Glu Glu Glu Lys
                85                  90                  95
Glu Glu Leu Ser Lys Ser Met Glu Asn Tyr Ser Ser Glu Phe Glu Ser
            100                 105                 110
Ala Val Lys Glu Ser Leu Asp Cys Cys Ser Gly Arg Lys Thr Met
        115                 120                 125
Glu Glu Thr Val Thr Ala Glu Glu Glu Lys Ala Lys Leu Met Thr
    130                 135                 140
Glu Met Pro Thr Glu Ser Glu Ile Glu Asp Phe Phe Val Glu Ala Glu
145                 150                 155                 160
Lys Gln Leu Lys Glu Lys Phe Lys Lys Tyr Asn Phe Asp Phe Glu
                165                 170                 175
Lys Glu Lys Pro Leu Glu Gly Arg Tyr Glu Trp Val Lys Leu Glu
            180                 185                 190

<210> SEQ ID NO 7
<211> LENGTH: 2116
<212> TYPE: DNA
<213> ORGANISM: Arabidopsis thaliana

<400> SEQUENCE: 7
aagcttttga attgtagata aatcatctgc tacagttata ccattatata tcttattaaa      60
gacctaagtt tccttcacta tacgtcttcg tccatttacg tacgtattat acggacggtt     120
taagctacta tatctatatt gttaacaatg taactgttga gatatatctt gcaataatat     180
gtcatggtgt atgcatacga taatatgaat caatgtttga aatcttgacg tgcccgtgat     240
acaataagat gatcaaaatt tcaaattttg tcaaatatta aacaacata cacatacaca      300
tgtgtccagg tggcattata aatgtatat atggtggata tagagagaga gggagatgcg      360
tatagtgaat aggaaagtaa gtaataaaga gagggtggag gaattggaaa ggggttggag      420
gcaaacccat aaagagcatt catttccttt taaggtcgct gaaattaatg agtaacgatc      480
ggtcaatgcc tctcgctgac cttttctctt tttacaaca acaaataaaa ataaaataaa       540
tttcgacgtc tctttccgct gctgaattac atttgttgaa ttaattttct ctgcttacgt      600
acgtcttcta aactttctct atccgaattc ttttttaact ttctaactta tattcaacaa      660
ctcttctttc ctgcctttac cgttagtcta attgttttcc taatactgct acgtacatac      720
ccctactata ctagtcagtg tattagattc gattgggatt aatccaggaa tatagatatc      780
ccattagttt ttataaaaat attggaagag acaagtctc aagcaattta gggttccatg      840
tagcgctgca atatactgtt agtaactctc tcttacccat atattgtata tgctaattct      900
tatcaaatat atatatatgc ttctcccaga gtcccagttt cctataatcc tgacgcaatt      960
atactaatag agccaagttt acataataaa gtatatatga ttaatagata gggtttctta     1020
ttaagccata tcttaaatta agatgtgatg atagcgtttt gtataagtta ccaattgttt     1080
gaaagaagag atcatcacaa taataaatca taagtagtag tatatagtaa taaataaata     1140
cacaagtcat aataagagta atgagaggat aattaaggag ggaagaagaa agcagaaaat     1200
gcggttggag aattaggtgc taaaagttag ttgagtccat ctcagtatct aacggtcaac     1260
tctctctctc tctagagaaa acaattaaga aatctgacat acacatatgt ctctctctct     1320
ctctctctct agtctataca cacaattcaa ttaaagaaga gacagagaag ttcgtctttt     1380
ttgtttttat acccttaaat caatcatgca attgtaaccc ttccttctta ttctcattcc     1440
ttccccccct gtctacagta atctatagca acgccattat gtactacttt taacggataa     1500
```

```
tttgctcatg tttcaatatg gcttcattgt atatatgttc aagttcttct caatcccttta    1560 tatcattcca acataattca tattaaagtt agtagctgaa attggaaggc tgatatattt    1620
tccataattc aaatttgaat tttgctcatc atatatatat gtatatatta aaaatcgaat    1680
attaagaaga aaaatgaagt cgatcgatgg ctgccaatgc tgtagctggc catgttttaa    1740
actactcaat tgtcggattg aagtatagcc aaaatatata aaccgtaaa aggactaaat     1800 ataataatat aataggtatt aattaattaa aactaattaa ttataaaaga agcacctaaa    1860
agtcaagagc agtagagaaa tggaagaaat atctgaaaaa cgaccgctta tatatatatg    1920
tatcattgga attgtagagg ctatatatat atatatatat atatatatat atatcgatct    1980
tagcttatat attaattgaa agtacatttt ggtgtataag taattaaaga agaaagaaaa    2040
aaagagagat aatatataag gaagaaggag tgcgaggaga agagggaaga gatcataatt    2100
aagcaaagaa gctagc                                                    2116

<210> SEQ ID NO 8
<211> LENGTH: 34
<212> TYPE: DNA
<213> ORGANISM: Artificial Sequence
<220> FEATURE:
<223> OTHER INFORMATION: primer

<400> SEQUENCE: 8
acctgcaggt gtaagttttg atcacatcct cttg                                34

<210> SEQ ID NO 9
<211> LENGTH: 30
<212> TYPE: DNA
<213> ORGANISM: Artificial Sequence
<220> FEATURE:
<223> OTHER INFORMATION: primer

<400> SEQUENCE: 9
agtcgacatc gctctcccaa tgattcttac                                     30

<210> SEQ ID NO 10
<211> LENGTH: 28
<212> TYPE: DNA
<213> ORGANISM: Artificial Sequence
<220> FEATURE:
<223> OTHER INFORMATION: primer

<400> SEQUENCE: 10
agagctctga atggaagaag cctgtttc                                       28

<210> SEQ ID NO 11
<211> LENGTH: 27
<212> TYPE: DNA
<213> ORGANISM: Artificial Sequence
<220> FEATURE:
<223> OTHER INFORMATION: primer

<400> SEQUENCE: 11
acccgggacg agaatcaacc ccgtgag                                        27
```

METHOD OF MODIFYING EPIDERMAL OUTGROWTH STRUCTURES VIA MODULATING CELL CYCLE CONTROL GENES

CROSS REFERENCE TO RELATED APPLICATIONS

This application claims priority to U.S. Provisional Application No. 60/381,510, filed May 17, 2002, which application is incorporated herein by reference.

FIELD OF INVENTION

The present invention relates generally to a method of modifying the morphological, biochemical, physiological properties or characteristics of plant epidermal outgrowth structures by modulating the expression of cell cycle control genes.

BACKGROUND OF THE INVENTION

The plant surface serves as an interface to the environment. Many substances from the outside are taken up by the plant and many internal products are released. In addition, some of these substances produced or taken up by the plant are also stored in surface structures. The interactions between the plant and its environment take place on the aerial surface such as the shoot, leaves, flowers, etc. as well as on the surface of the root. The surface of plants is built by the epidermis, a tissue in which highly specialized cells are formed to accomplish the various above sketched functions. Examples of these specialized cell types are e.g. plant hairs (trichomes), which are involved in protection against insects or other pathogens by either secretion of substances or steric hindrance, root hairs which mediate nutrient and water uptake, or stomata which regulate gas exchange. Trichomes are single-celled hairs that during wild-type maturation undergo an average of four rounds of endoreduplication, leading to a characteristic 3-4-branched cell with a DNA content of approximately 32C. See Hulskamp et al., Int. Rev. Cytol., 186, 147-178 (1999) and Traas et al., Curr. Opin. Plant Biol., 1, 498-503 (1998). Mutant trichomes with a lesser DNA content (e.g., 16C) are smaller and have fewer branches, whereas trichomes with a higher DNA content (e.g., 64C) are larger and develop more branches.

Due to their metabolic activities, many of the epidermal cells of various plants are of economical interest. An alteration of the cell number, size, or other cellular parameters can influence the metabolic power and thus their economical use.

SUMMARY OF THE INVENTION

The present invention provides a method of modifying the morphological, biochemical, physiological properties or characteristics of a plant epidermal outgrowth structure. The method comprises modulating expression of one or more cell cycle control genes in the epidermal outgrowth structure.

Examples of cell cycle control genes which may be used in the methods of the present invention include but are not limited to D-type cyclins, B-type cyclins, A-type cyclins, E2F-DP transcription factors, CDC20 homologs, CDH1 homologs, CDC25 homologs, WEE1 homologs, cyclin dependent kinase inhibitors (CKI) such as KRP, MAP kinases, or PIP kinases.

Preferably, the B-type cyclin used in the methods of the present invention is CYCB1;2 (MIPS Accession No. At5g06150) and the D-type cyclin used in the methods of the present invention is CYCD3;1 (MIPS Accession No. At4g34160)

Epidermal outgrowth structures which may be modified in accordance with the present invention include aerial (above ground) structure such as e.g., trichomes (plant hairs). Subterrestrial outgrowth structures may also be modified such as e.g., root hairs.

A method for identifying cell cycle control genes capable of modifying the morphological, biochemical, physiological properties or characteristics of a plant epidermal outgrowth structure is also provided. The method comprises the steps of: transforming a plant with a cell cycle control gene operably linked to an epidermis-preferred promoter; monitoring changes in the morphological, biochemical, physiological properties or characteristics of plant epidermal outgrowth structure of said transformed plant relative to corresponding wild-type plants; and identifying cell cycle genes capable of modifying morphological, biochemical, physiological properties or characteristics of plant epidermal outgrowth structures.

Also provided are transgenic plants which ectopically express a cell cycle control protein in an epidermal outgrowth structure. Such transgenic plants exhibit modified morphological, biochemical, or physiological properties or characteristics in the epidermal outgrowth structure.

In accordance with the present invention, there is also provided a method for producing a plant having a modified epidermal outgrowth structure. The method comprises: transforming a plant cell with a cell cycle control gene operably linked to an epidermis-preferred promoter and regenerating a plant from the transformed plant cell, wherein the regenerated plant has a modified epidermal outgrowth structure. Plants having a modified epidermal outgrowth structure produced by the above-described method are also provided.

(a) Scanning electron micrograph of single-celled mature wild-type trichomes. (b) Scanning electron micrograph of multicellular pGL2::CYCD3;1#1 trichomes. (c) Four consecutive sections through a multicellular pGL2:: CYCD3;1#1 trichome revealing many separate cells. (d) Scanning electron micrograph of pGL2::CYCD3;1#2 trichomes that have a lower rate of multicellular trichomes in comparison to line 1. (e) Light micrograph of 4', 6-diamidino-2-phenylindole-stained trichomes of pGL2::CYCD3;1-pGL2::CYCB1;2 plants showing strong synergistic phenotype with up to 80 nuclei per trichome initiation site (TIS); similar trichomes arise by the expression of pGL2::CYCD3;1 in a homozygous sim mutant background. (f) Staining of pGL2::CYCD3;1 trichomes revealing the expression of the trichome marker line pGL2::GUS. (g) Staining of pGL2:: CYCD3;1 trichomes (arrows) revealing the expression of the trichome marker line pGL1::GUS.

Figure 2:
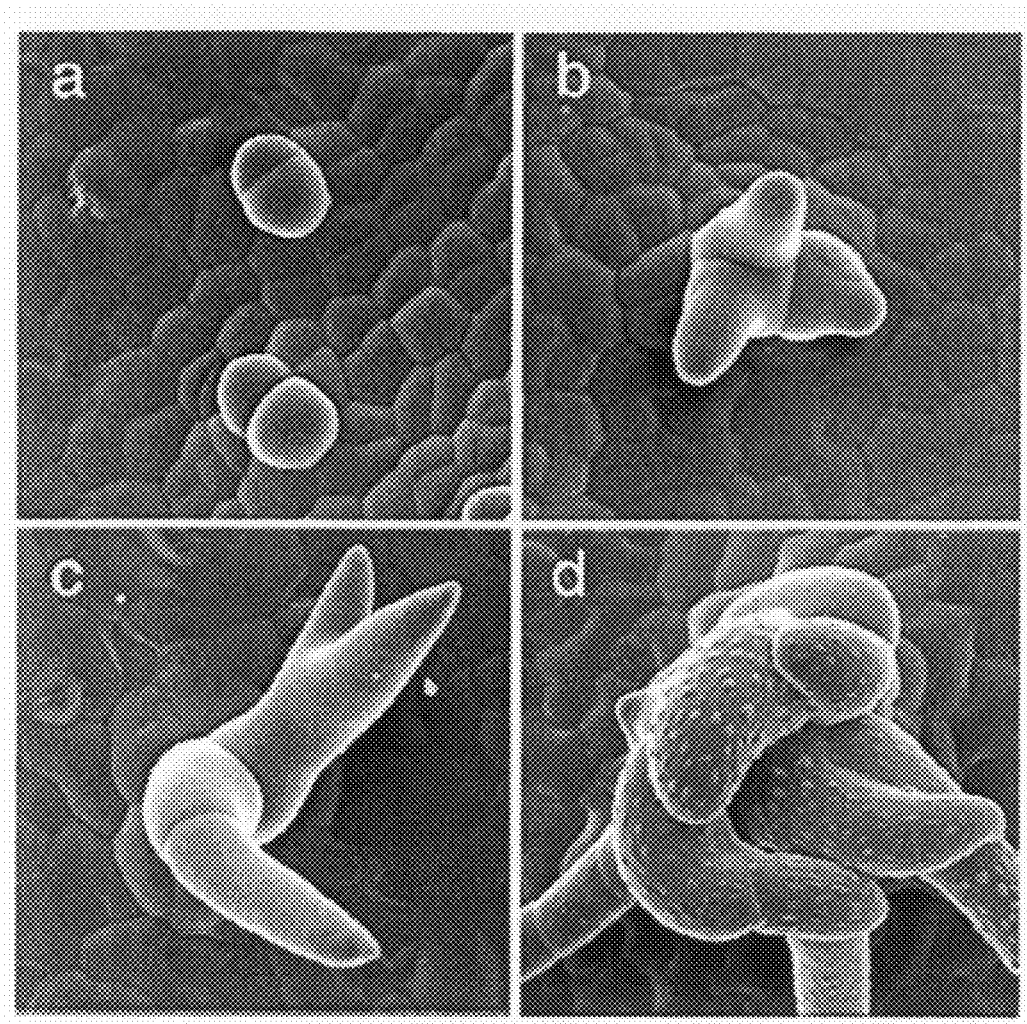

FIG. 2: Analysis of pGL2::CYCD3;1 trichome development.

(a-d) Scanning electron micrographs of pGL2::CYCD3;1 trichomes. (a) Very young dividing trichomes giving rise to trichome clusters. (b and c) Further cell divisions take place as trichomes grow out and elongate. (d) Mature multicellular trichome comprising many cells. Note that the individual cells form papillae.

Figure 3:
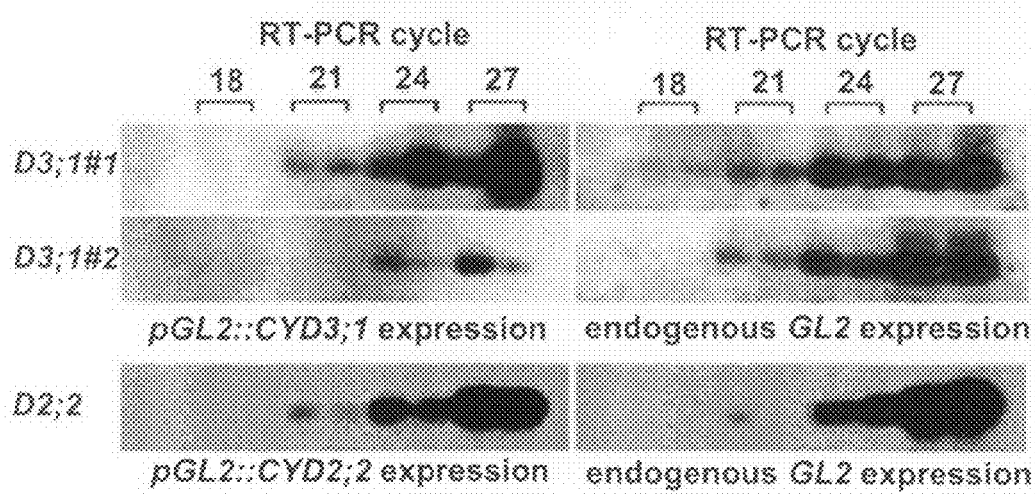

FIG. 3: Transgene expression analysis.

Semiquantitative RT-PCR showing the relative expression strength of pGL2::CYCD3;1 in lines 1 (D3;1#1) and #2 (D3; 1#2) and pGL2::CYCD2;2 (D2;2) in comparison with endogenous GLABRA 2 (GL2) expression; 18, 21, 24, and 27 indicate the RT-PCR cycle numbers. In pGL2::CYCD3;1#1, CYCD3;1 is expressed at least 10-fold stronger than in line 2. The expression strength of pGL2::CYCD2;2 is slightly less than pGL2::CYCD3;1#1 but approximately 10-fold stronger than in pGL2::CYCD3;1 #2.

Figure 4:
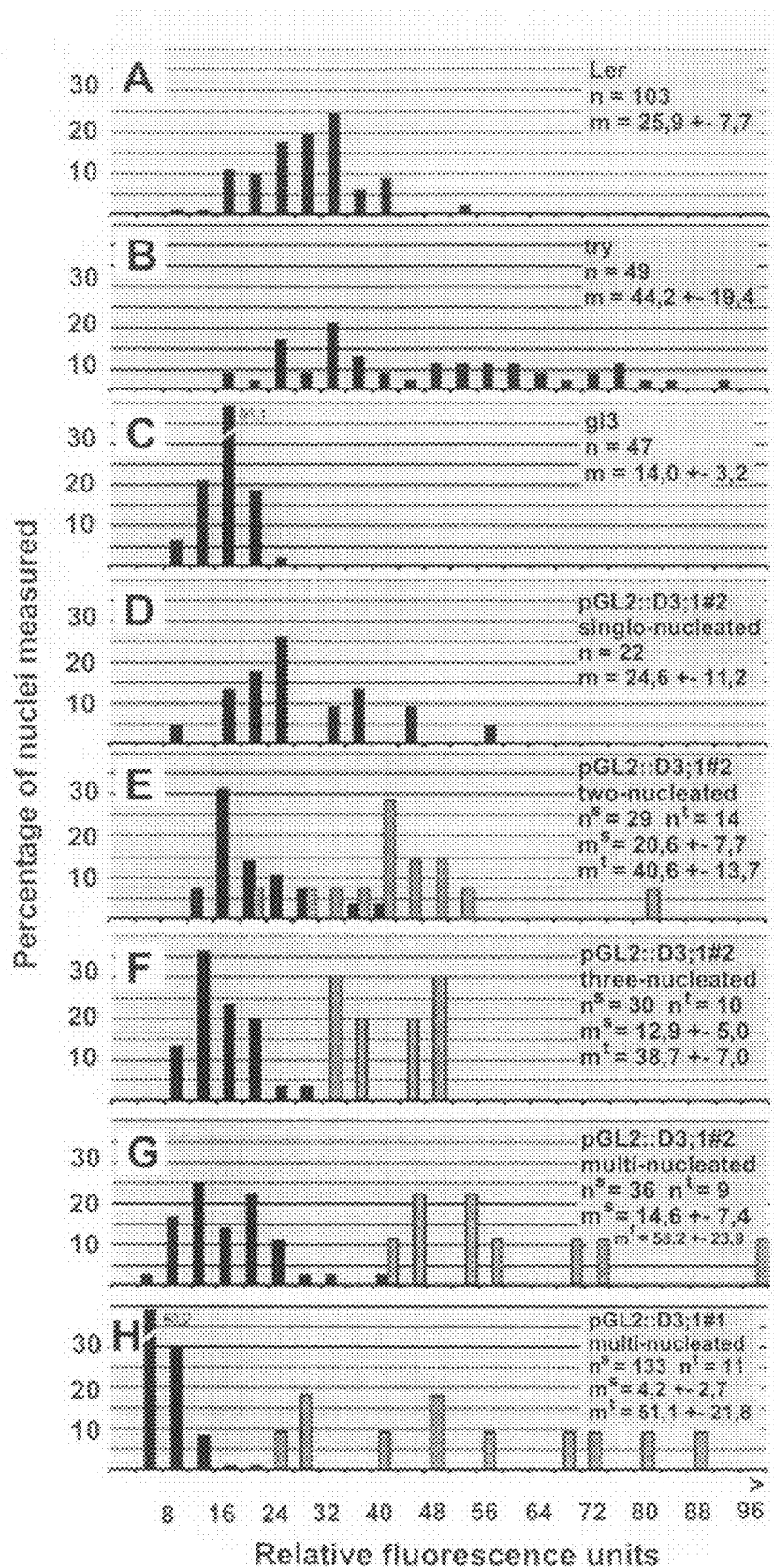

FIG. 4: Analysis of DNA content.

(a-f) Distribution of DNA contents given in relative fluorescence units of the single nuclei (black bar) and the sum of all nuclei per trichome initiation site (TIS)—light bar)). The relative, fluorescence units are calibrated with wild-type, triptychon, and glabra 3 trichome nuclei such that 2 relative fluorescence units roughly represent 2C by defining the major peak in the wild-type trichomes as 32C and the major peak in glabra 3 as 16C in accordance to previously measured trichome nuclei (9, 23, 34). The mean (m) is given for the single nuclei ($m^s$) and the total DNA contents as the sum of all nuclei per TIS ($m^t$). (a) Wild type. (b) triptychon (try). (c) glabra3 (gl3). (d) Single-nucleated pGL2::CYCD3;1#2 trichomes. (e) Two-nucleated pGL2::CYCD3;1#2 trichomes. (j) Three-nucleated pGL2::CYCD3;1#2 trichomes. (g) pGL2:: CYCD3;1#2 trichomes with more than three nuclei. (h) pGL2::CYCD3;1#1 trichomes with more than three nuclei.

Figure 5:
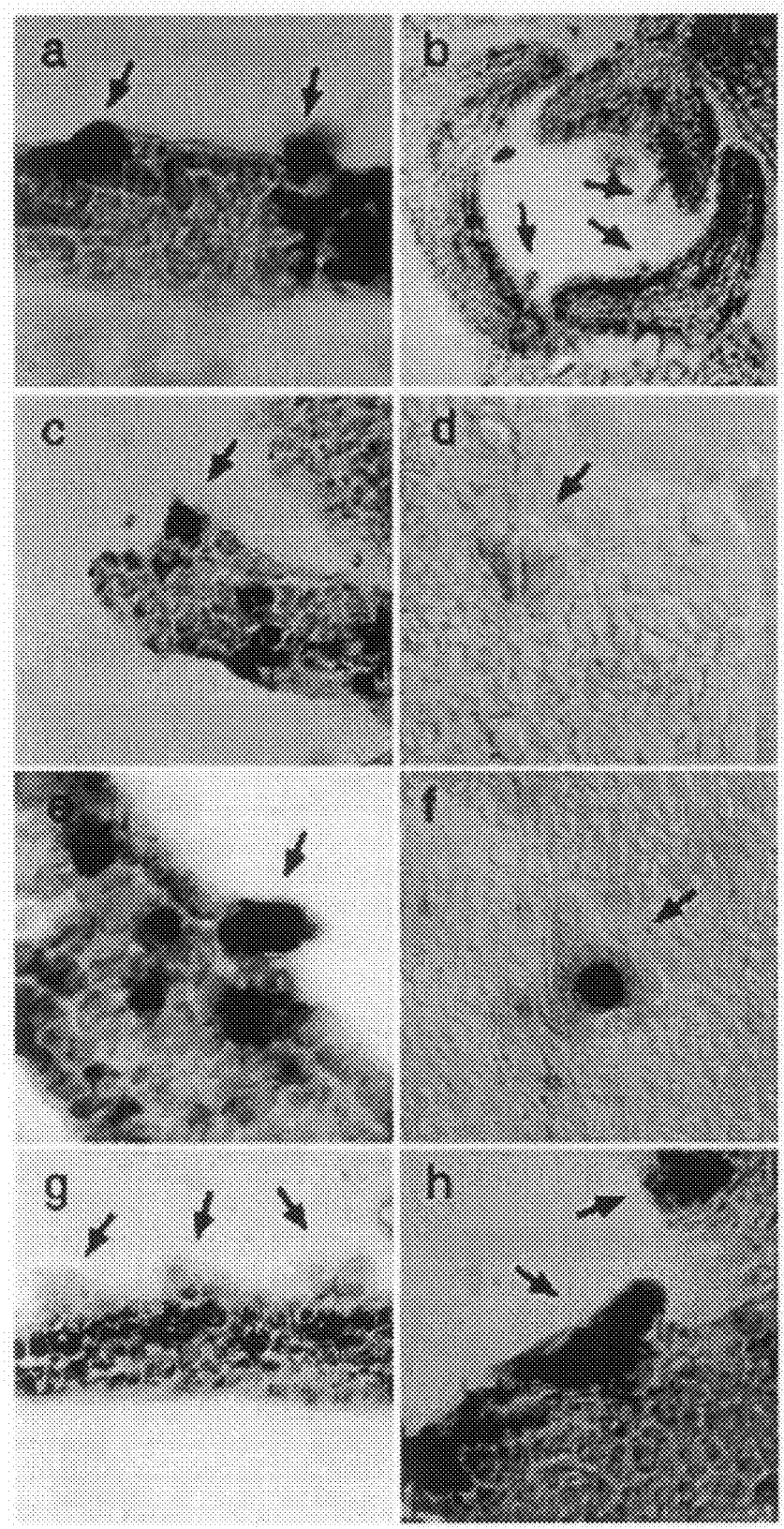

FIG. 5: Expression analysis.

(a) Strong staining with the CYCD3;1 antisense probe in pGL2::CYCD3;1 trichomes (arrows); no signal was obtained with the CYCD3;1 sense probe (data not shown). (b) Detection of CYCD3;1 mRNA in young leaves with no staining in trichomes (arrows). (c) Detection of CYCB1;1 mRNA in pGL2::CYCD3;1 trichomes (arrows). (d) Staining of trichomes expressing pCYCB1;1::GUS in pGL2::CYCD3;1 plants. (e) Detection of CYCB1;2 mRNA in pGL2:: CYCD3;1 trichomes (arrows). (f) Staining of trichomes expressing pCYCB1;2::GUS in pGL2::CYCD3;1 plants. (g) No detection of CYCD3;1 mRNA in sim mutant trichomes (arrows). (h) Detection of GL2 mRNA in sim mutant trichomes (arrows).

Figure 6:
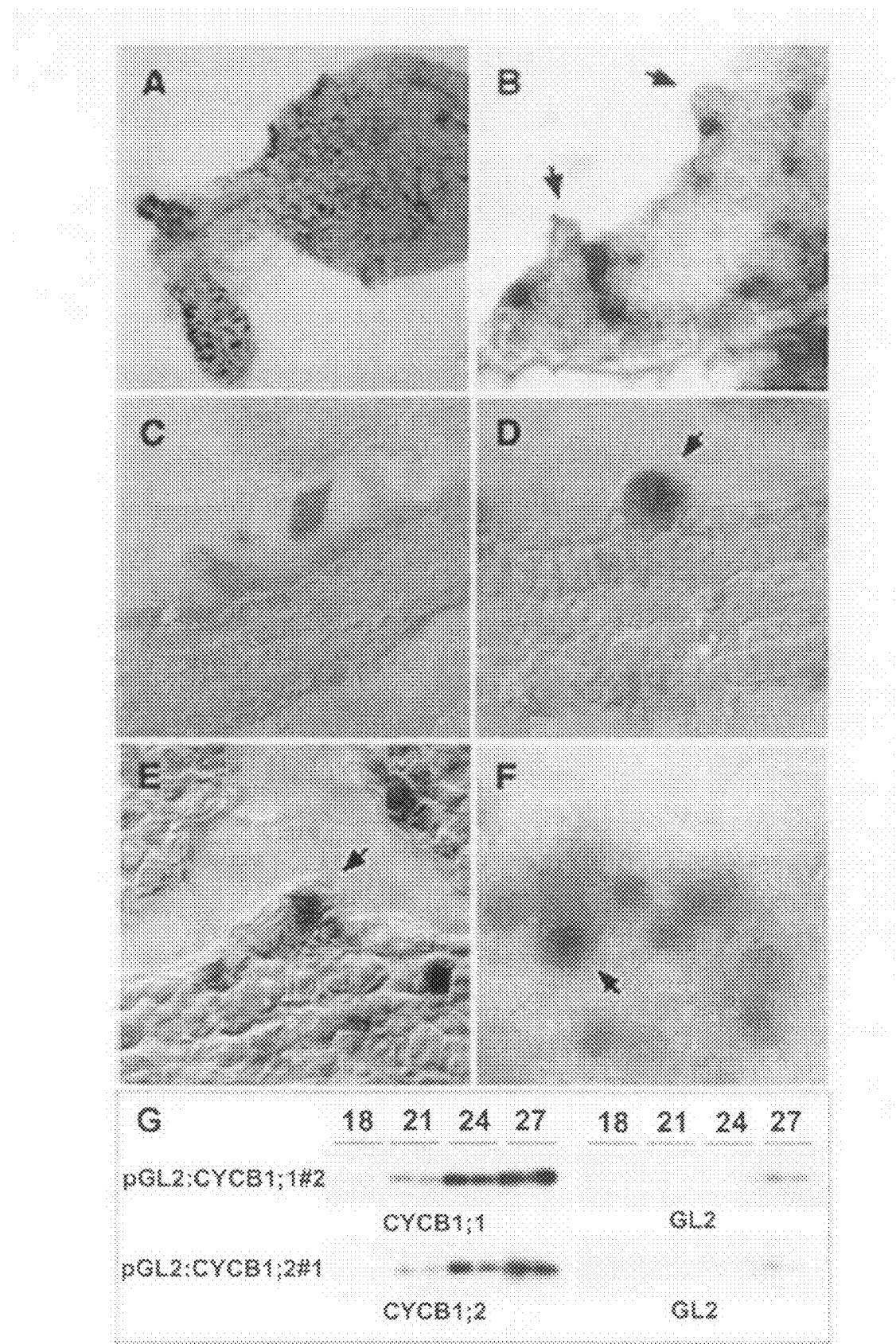

FIG. 6: Expression analysis of CYCB1;2

(A) "Salt and pepper" staining of young leaves expressing pCYCB1;2::GUS in wild-type.

(B) Detection of CYCB1;2 mRNA in a "salt and pepper" pattern of young leaf cells in wild-type, no detection in trichomes (arrowhead).

(C) No specific staining with a sense probe of CYCB1;2 in wild type.

(D) Detection of CYCB1;2 mRNA in pGL2::CYCB1;2 trichomes (arrowheads).

(E) Detection of KN mRNA in pGL2::CYCB1;2 trichomes.

(F) pCYCB1;2::GUS staining in sim trichomes (arrowheads).

(G) Semi-quantitative RT-PCR showing the relative expression strength of pGL2::CYCB1;1 in comparison to pGL2:: CYCB1;2; 18, 21, 24 and 27 indicate the RT-PCR cycle number. As a standard, the endogenous GL2 expression was used; note that, whereas both cyclin probes were equally strong, the GL2 label was less potent.

Figure 7:
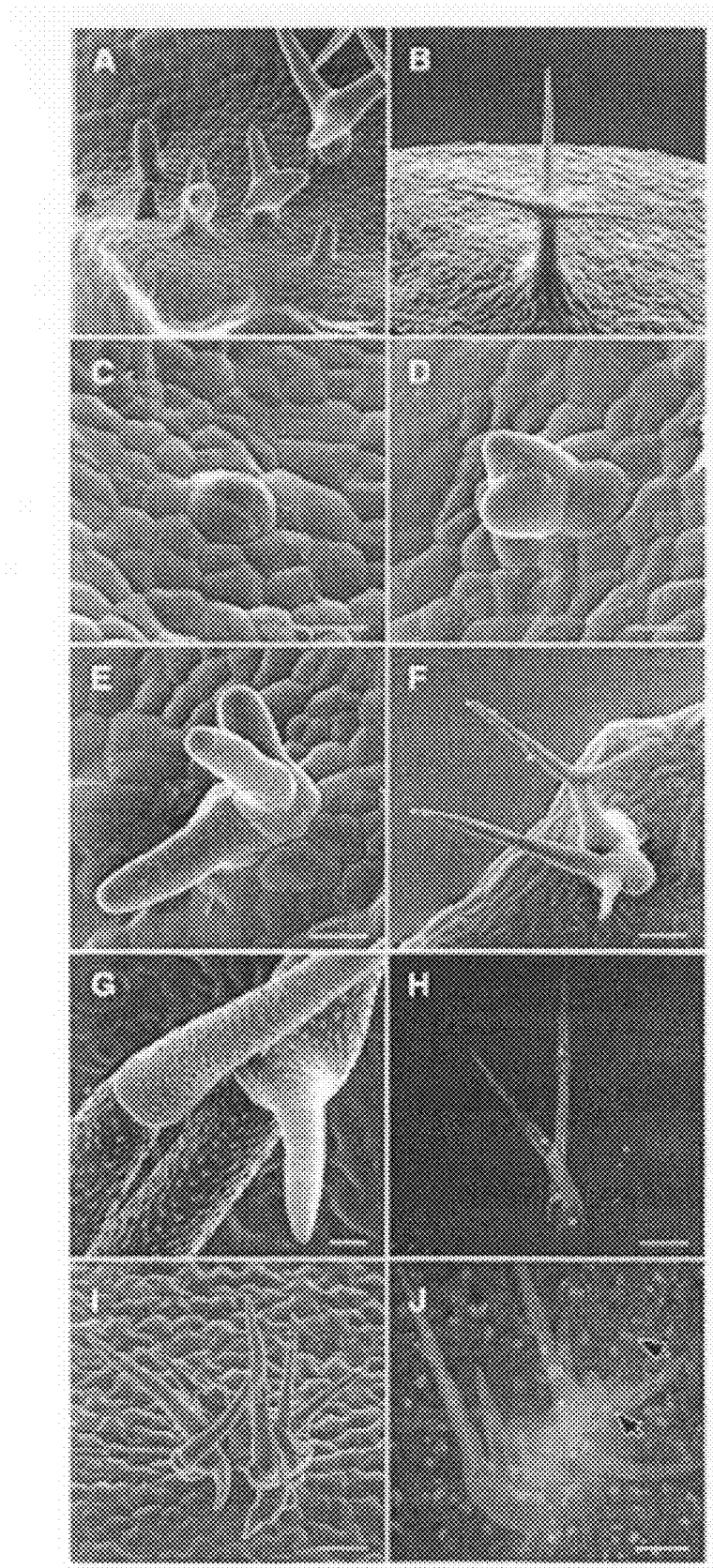

FIG. 7: Morphological analysis (A) A scanning electron micrograph of wild-type trichomes developing at the base of a rosette leaf; the scale bar represents 30 µm.

(B) A mature wild-type trichome; the scale bar represents 100 µm.

(C-E) Development of pGL2::CYCB1;2 trichomes; the scale bar represents 10 µm.

(F) A mature pGL2::CYCB1;2 trichome; the scale bar represents 30 µm.

(G) A close-up view of a constriction on a pGL2::CYCB1;2 trichome showing a cell border; the scale bar represents 10 µm.

(H) A confocal scanning micrograph of a CYTO13-stained pGL2::CYCB1;2 multinucleated trichome; the scale bar represents 100 µm.

(I) A scanning electron micrograph of pGL2::CYCB1;2 trichomes in sim mutant background; the scale bar represents 30 µm.

(J) A light micrograph of DAPI-stained trichomes in pGL2:: CYCB1;2 in sim, the scale bar represents 30 µm. Some nuclei of a multinucleated trichome (arrowhead) appear larger than the 2C nuclei of the surrounding stomata cells.

Figure 8:
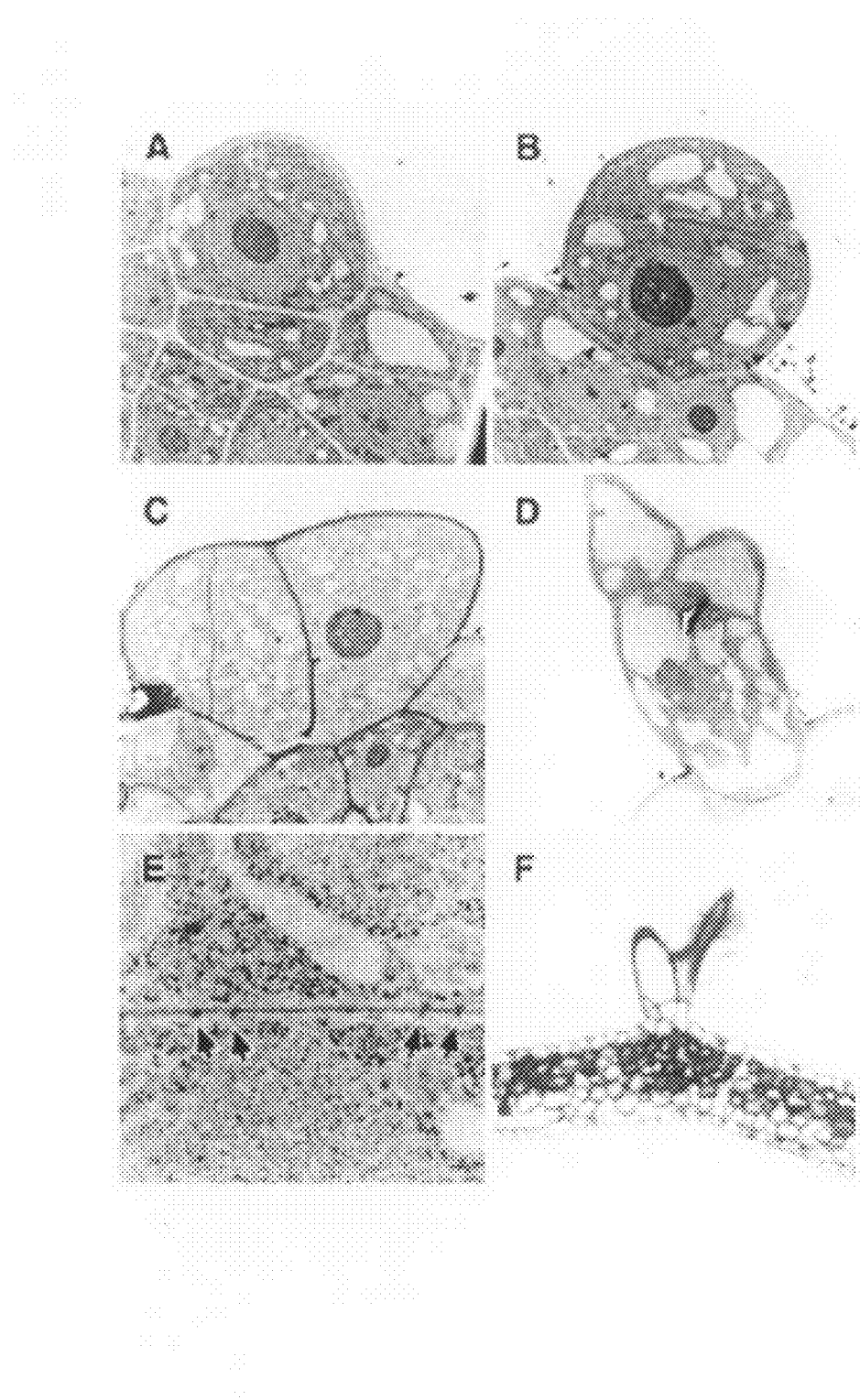

FIG. 8: Ultrastructural Analysis of pGL2::CYCB1;2 trichomes (A) A single-celled trichome.

(B-C) Developing multicellular trichomes with a newly formed cell wall showing no obvious differences to cell walls in the epidermis.

(D) A mature multicellular trichome.

(E) Plasmodesmata in the cell wall within a multicellular trichome (arrowhead).

(F) A semithick section of a mature multicellular trichome.

Figure 9:
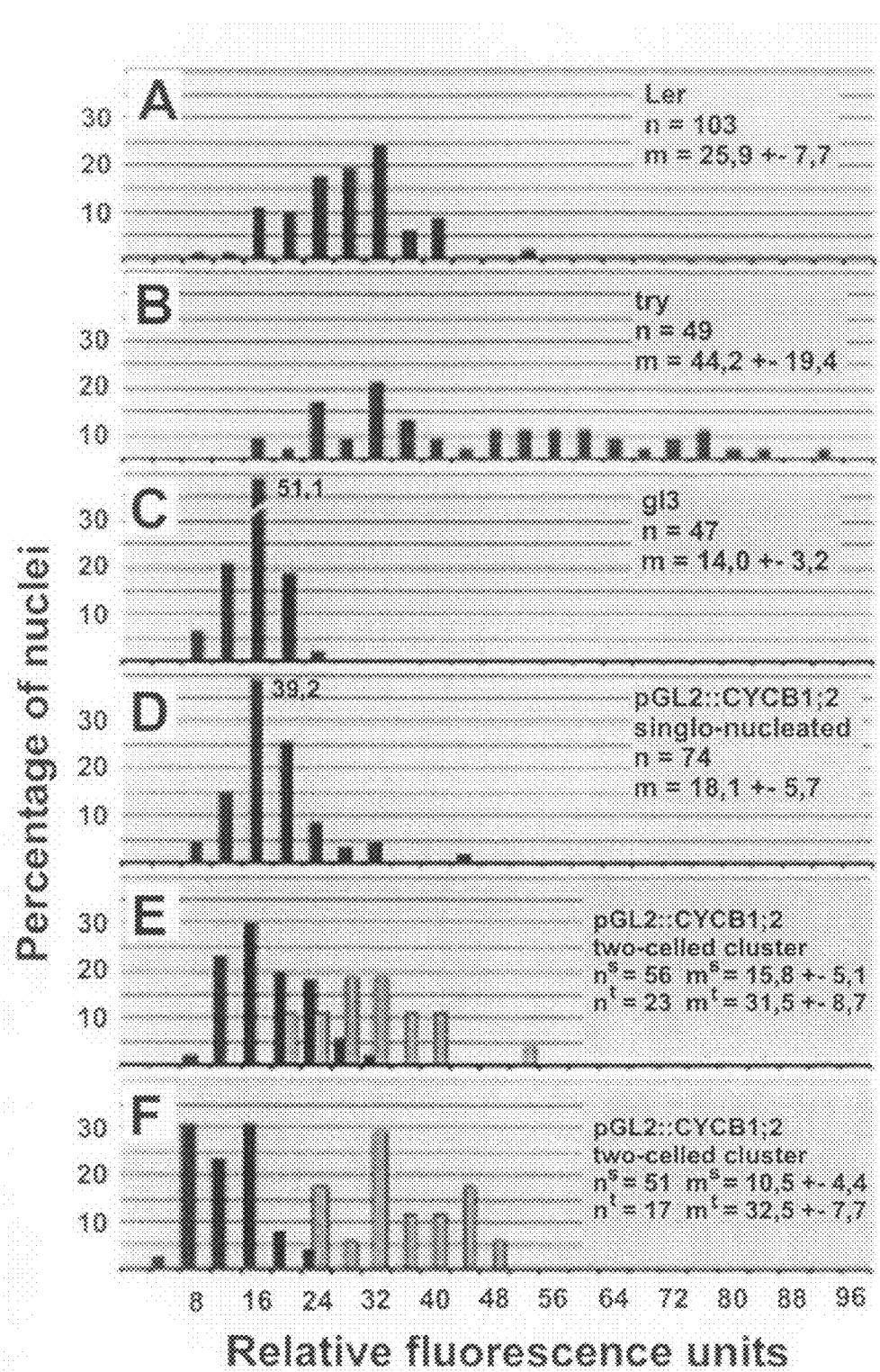

FIG. 9: Analysis of DNA Content and Number of Nuclei (A-F) Distribution of the DNA contents given in relative fluorescence units (RFU) of the single nuclei (black bar) and the sum of all nuclei per TIS (light bar). The RFU are calibrated with wild-type, triptychon, glabra3 trichome nuclei so that 2 RFU roughly represents 2C by defining the major peak in the wild-type trichomes as 32C and the major peak in glahra3 as 16C, in accordance to previously measured trichome nuclei [9, 25, 29]. The mean (m) is given for the single nuclei ($m^s$) and the total DNA contents as the sum of all nuclei per TIS ($m^t$). (A) Wild type. (B) Triptychon (Try). (C) Glabra3 (gl3). (D) Single-celled pGL2::CYCB1;2 trichomes. (E) Two-celled clusters of pGL2::CYCB1;2 trichomes. (F) Three-celled clusters of pGL2::CYCB1;2 trichomes.

Figure 10:
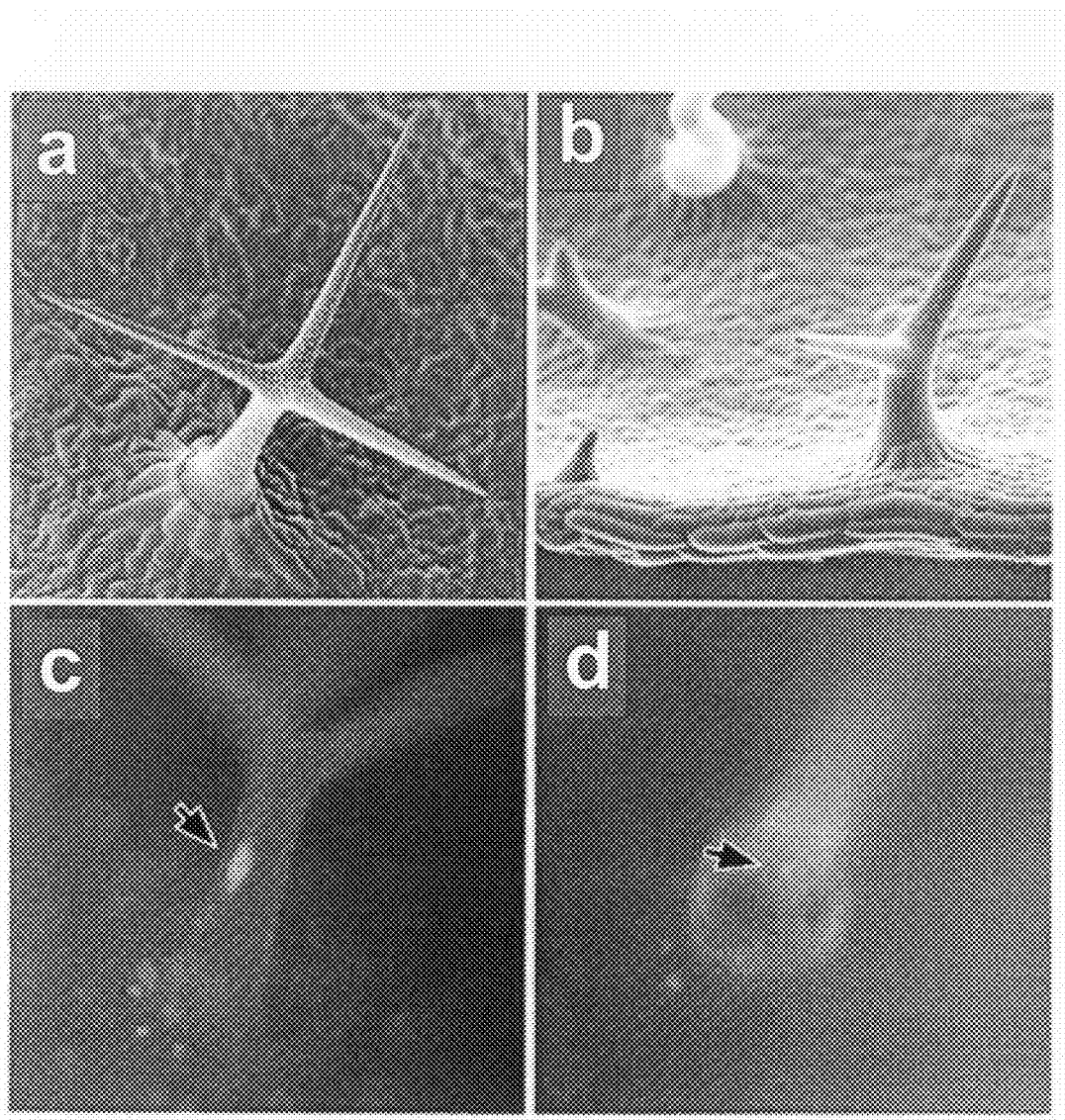

FIG. 10: a, Electron micrograph of a three-branched wild-type *Arabidopsis* trichome. b, Electron micrograph of a trichome expressing KRP1. The trichome cell size is reduced and the trichomes have less branches. c, DAPI staining of a wild-type *Arabidopsis* trichome; arrow marks the endoreduplicated nucleus. d, DAPI staining of a trichome expressing KRP1; the nucleus is reduced indicating a reduced endoreduplication level.

Figure 11:
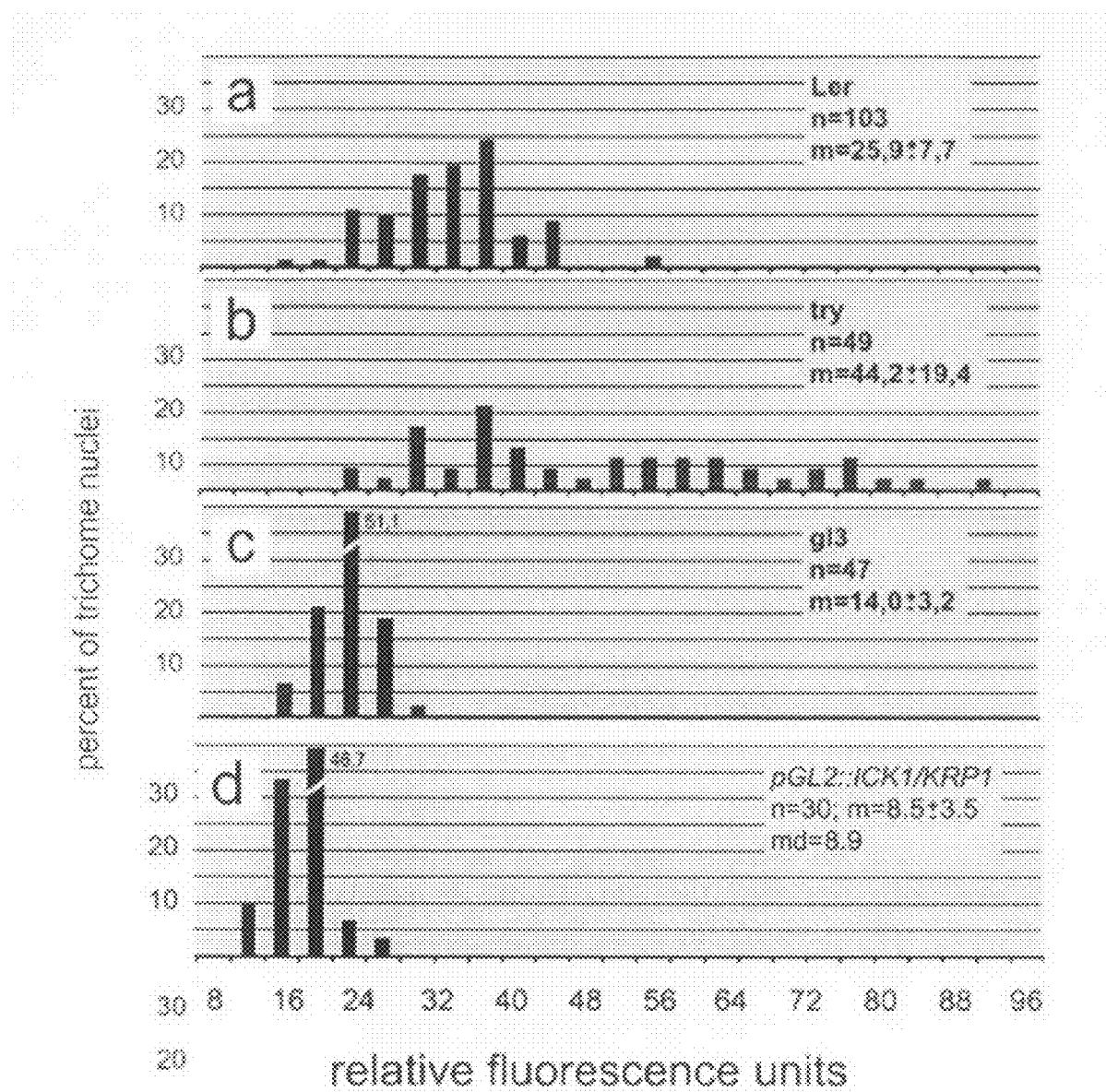

FIG. 11: a-d, Distribution of DNA contents given in relative fluorescence units (RFU) of trichome nuclei. The RFU are calibrated with wild-type, triptychon, and glabra 3 trichome nuclei so that 2 RFU roughly represents 2C by defining the major peak in the wild-type trichomes as 32 C and the major peak in glabra 3 as 16 C in accordance to previously measured trichome nuclei. The mean (m) is given for the nuclei (m). a, Wild type. b, triptychon (try). c, glabra 3 (gl3). d, pGL2::KRP1 trichomes. KRP expressing trichomes have in comparison to wild-type a much reduced DNA content, even less than in the glabra3 mutant.

DESCRIPTION OF THE INVENTION

In accordance with the present invention, it has been discovered that expression of cell cycle control genes can modify the cell size, morphology and thus the biochemical and physiological properties of epidermal outgrowth structures. An important feature is the expression of cell cycle control genes in a cell-type specific manner by using cell specific promoters or promoters which show a preference to epidermal structures.

The term "promoter" as used herein, is to be taken in a broad context to refer to regulatory nucleic acid sequences capable of effecting expression of the sequences to which they are operably linked. Encompassed by the term are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a–35 box sequence and/or–10 box transcriptional regulatory sequences. The term also encompasses a synthetic fusion molecule or derivative which confers, activates or enhances expression of a nucleic acid molecule in a cell, tissue or organ. The term "operably linked" as used herein refers to a functional linkage between the promoter sequence and the gene of interest, such that the promoter sequence is able to initiate transcription of the gene of interest.

The term "cell-type specific" refers not only to exclusive expression of the respective promoter in one cell type in one developmental condition but is also used in a broader sense to include other cell types which show expression and/or where the expression pattern changes during development. The term "cell specific promoter" is meant to include promoter sequences found in nature, including natural promoter sequences comprising one or more mutations (additions, deletions, and/or substitutions of nucleotides) as well synthetic promoters, i.e. the combination of different regulatory elements. The cell-type specific promoter contrasts an ubiquitous expression in all or many cell types. Constructs with an ubiquitous expression often interfere with the viability and/or fertility of the plant. A second effect of that is, that there is often a strong counterselection against ubiquitous expression constructs resulting in transgenic plants with only comparatively low expression level.

As used herein, an "epidermis-preferred" promoter directs expression predominantly, but not exclusively, in epidermal outgrowth structures.

A cell type specific expression of cell cycle control genes is achieved by building a specific expression construct. An increasing number of promoter elements for such a construct are available. With fast-growing compiling of information for the genomes of different plant species, many promoter elements have been and will be described in the future. Predominantly, regulatory elements reside in the 5'untranslated region (5'UTR) of a given gene. In accordance with the present invention, the promoter directing expression of the cell cycle control protein does not have to be switched on throughout the entire life of the plant cell or life cycle of the plant.

In addition, elements might occur in the introns or in the 3'untranslated region (3'UTR). Examples of regulatory elements which may be used in accordance with the present invention include but are not limited to those listed in Table 1.

TABLE 1

Exemplary promoters with an expression preference to epidermal structures

| Promoter | Epidermal structure | Reference |
|---|---|---|
| LIPID TRANSFER PROTEIN 3 (LTP3) from Cotton | Trichome | Liu et al., 2000, Biochim Biophys Acta. Aug. 24, 1487(1): 106-11 |
| GLABRA2 (GL2) from Arabidopsis | Trichome, non-root-hair cells, integuments | Szymanski et al., 1998, Development Apr; 125(7): 1161-71 |
| GORK from Arabidopsis | Root-hairs | Ivashikina et al., 2001, FEBS Lett. Nov 23; 508(3): 463-9 |
| MIP-MOD from Brassica | Stigma | Dixit et al., 2001, Plant Mol Biol. Jan; 45(1): 51-62 |
| BLEC4 from pea (Pisum sativum), also active in alfalfa | Epidermis | Mandaci et al., 1997, Plant Mol Biol. Aug; 34(6): 961-5 |
| WAXD9 from broccoli | Epidermis | Pyee et al., 1995, Plant J Jan; 7(1): 49-59 |
| MtENOD12 from Medicago truncatula | Root epidermis | Pichon et al., 1992, Plant Cell. Oct; 4(10): 1199-211 |

The pool of described regulatory elements can be increased further by two procedures. Firstly, it is possible to transfer regulatory elements between plant species which often maintain their expression characteristics (Mandaci and Dobres, 1997). In addition, regulatory elements can be combined to result in a synthetic promoter with the favoured expression pattern.

The regulatory elements are then combined by molecular procedures with the coding sequences for cell cycle control genes (Sambrook et al., 1989; Ausubel, 1994). Cell cycle control genes are genes which are either part of the core cell cycle machinery or influence or control this machinery. As with regulatory elements, cell cycle genes from one species have potentially the same function in the other organisms (Cockcroft et al., 2000). Examples of cell cycle control genes which may be used in accordance with the present invention include but are not limited to genes encoding: D-type cyclins, B-type cyclins, A-type cyclins, E2F-DP transcription factors, CDC20 and CDH1 homologues, CDC25 homologues, WEE1 homologues, KRPs and other cyclin dependent kinase inhibitors, MAP kinases, and PIP kinases. Such sequences are known and readily available from different plant species, yeasts, and animals. Preferably, a cell cycle control gene is from a plant. More preferably, the cell cycle control gene is isolated from a dicotyledonous species, preferably from the family Brassicaceae, more preferably from Arabidopsis thaliana. The cell cycle control gene may be substantially modified from its native form in composition and/or genomic environment through deliberate human manipulation. Most preferably, the nucleic acid is: (i) as represented by any of SEQ ID NO: 1, SEQ ID NO: 3, SEQ ID NO: 5 or a portion of any of the aforementioned sequences; or (ii) a nucleic acid sequence capable of hybridising with any of the aforementioned sequences; or (iii) a nucleic acid sequence encoding an amino acid sequence represented by any of SEQ ID NO: 2, SEQ ID NO: 4, SEQ ID NO: 6 or a homologue, derivative or active fragment of any of the aforementioned sequences. SEQ ID NO: 1 depicts the CYCD3;1 nucleic acid sequence (MIPS Accession No. At4g34160). SEQ ID NO: 2 depicts the corresponding amino acid sequence for SEQ ID NO: 1. SEQ ID NO:3 depicts the CYCB1;2 nucleic acid sequence (MIPS Accession No. At5g06150). SEQ ID NO: 4 depicts the corresponding amino acid sequence for SEQ ID NO: 3.

SEQ ID NO: 5 depicts the nucleic acid sequence for KRP1 (MIPS Accession No. At2g23430) and SEQ ID NO: 6 depicts the corresponding amino acid sequence.

Advantageously, the method according to the present invention may also be practised using portions of a sequence represented by any of SEQ ID NO: 1, SEQ ID NO: 3 or SEQ ID NO: 5 or by using sequences that hybridize (preferably under stringent conditions) to any of the aforementioned sequences (which portions or hybridising sequences encode cell cycle control proteins), or by using homologues, derivatives or active fragments of a sequence according to any of SEQ ID NO: 2, SEQ ID NO: 4 or SEQ ID NO: 6.

Phenotypic analysis (by light microscope, laser scanning confocal microscope, and other techniques) shows that expression of the CYCLIN B1;2 results in multicellular plant hairs whereas wild-type trichomes are always unicellular. Due to early divisions also the pattern of trichome distribution is altered. Many trichome arise now in clusters probably due to early divisions prior to trichome outgrowth. Interestingly, the total DNA content of wild-type and CYCLIN B1;2 expressing cells seems to be constant. Also the number of cells induced by CYCLN B1;2 expression had no influence on the total DNA content per multicellular trichome arguing that CYCLIN B1;2 acts downstream of factors controlling the cell cycle numbers. For further methodology and details see Schnittger et al. (Current Biology, Vol. 12, 415-420, Mar. 5, 2002) which is incorporated herein by reference as if fully set forth.

Phenotypic analysis (by light microscope, laser scanning confocal microscope, and other techniques) shows that expression of the CYCLIN D3;1 results in multicellular hairs whereas wild-type *Arabidopsis* trichomes are always unicellular. In contrast to CYCLIN B1;2 expression CYCLIN D3;1 also causes an increased total DNA content of the trichome structure. Interestingly, the overall trichome cell mass increased by CYCLIN D3;1 expression due to neoplesia (induction of new cell divisions). The induced cell divisions had no influence on the trichome fate, apparently all cells in a multicellular trichome adopt a trichome fate. For further methodology and details see Schnittger et al. (PNAS, Vol. 99, No. 9, Apr. 30, 2002, pp 6410-6415) which is incorporated herein by reference as if fully set forth.

Methods for the search and identification of homologues would be well within the realm of a person skilled in the art. Methods for the alignment of sequences for comparison are well known in the art, such methods include GAP, BESTFIT, BLAST, FASTA and TFASTA. GAP uses the algorithm of Needleman and Wunsch (J. Mol. Biol. 48: 443-453, 1970) to find the alignment of two complete sequences that maximises the number of matches and minimises the number of gaps. The BLAST algorithm calculates percent sequence identity and performs a statistical analysis of the similarity between the two sequences. The software for performing BLAST analysis is publicly available through the National Centre for Biotechnology Information.

"Homologues" encompass peptides, oligopeptides, polypeptides, proteins and enzymes having amino acid substitutions, deletions and/or insertions relative to the unmodified protein in question and having similar biological and functional activity as the unmodified protein from which they are derived. To produce such homologues, amino acids of the protein may be replaced by other amino acids having similar properties (such as similar hydrophobicity, hydrophilicity, antigenicity, propensity to form or break α-helical structures or β-sheet structures). Conservative substitution tables are well known in the art (see for example Creighton (1984) Proteins. W.H. Freeman and Company). The homologues useful in the method according to the invention have at least 25% sequence identity in the case of homologues of KRPs, at least 50% sequence identity or similarity (functional identity) to the unmodified protein in the case of other cell cycle control genes, alternatively at least 60% sequence identity or similarity to an unmodified protein, alternatively at least 70% sequence identity or similarity to an unmodified protein. Typically, the homologues have at least 80% sequence identity or similarity to an unmodified protein, preferably at least 85% sequence identity or similarity, further preferably at least 90% sequence identity or similarity to an unmodified protein, most preferably at least 95% sequence identity or similarity to an unmodified protein.

Two special forms of homology, orthologous and paralogous, are evolutionary concepts used to describe ancestral relationships of genes. The term "paralogous" relates to gene-duplications within the genome of a species leading to paralogous genes. The term "orthologous" relates to homologous genes in different organisms due to ancestral relationship. The term "homologues" as used herein also encompasses paralogues and orthologues of the proteins useful in the methods according to the invention.

"Substitutional variants" of a protein are those in which at least one residue in an amino acid sequence has been removed and a different residue inserted in its place. Amino acid substitutions are typically of single residues, but may be clustered depending upon functional constraints placed upon the polypeptide; insertions will usually be of the order of about 1-10 amino acid residues, and deletions will range from about 1-20 residues. Preferably, amino acid substitutions comprise conservative amino acid substitutions.

"Insertional variants" of a protein are those in which one or more amino acid residues are introduced into a predetermined site in a protein. Insertions can comprise amino-terminal and/or carboxy-terminal fusions as well as intra-sequence insertions of single or multiple amino acids. Generally, insertions within the amino acid sequence will be smaller than amino- or carboxy-terminal fusions, of the order of about 1 to 10 residues. Examples of amino- or carboxy-terminal fusion proteins or peptides include the binding domain or activation domain of a transcriptional activator as used in the yeast two-hybrid system, phage coat proteins, (histidine)$_6$-tag, glutathione S-transferase-tag, protein A, maltose-binding protein, dihydrofolate reductase, Tag-100 epitope, c-myc epitope, FLAG®-epitope, lacZ, CMP (calmodulin-binding peptide), HA epitope, protein C epitope and VSV epitope.

"Deletion variants" of a protein are characterised by the removal of one or more amino acids from the protein. Amino acid variants of a protein may readily be made using peptide synthetic techniques well known in the art, such as solid phase peptide synthesis and the like, or by recombinant DNA manipulations. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

The term "derivatives" refers to peptides, oligopeptides, polypeptides, proteins and enzymes which may comprise substitutions, deletions or additions of naturally and non-naturally occurring amino acid residues compared to the amino acid sequence of a naturally-occurring form of the protein, for example, as presented in SEQ ID NO: 2. "Derivatives" encompass peptides, oligopeptides, polypeptides, proteins and enzymes which may comprise naturally occurring altered, glycosylated, acylated or non-naturally occurring amino acid residues compared to the amino acid sequence of a naturally-occurring form of the polypeptide. A derivative may also comprise one or more non-amino acid substituents compared to the amino acid sequence from which it is derived, for example a reporter molecule or other ligand, covalently or non-covalently bound to the amino acid sequence such as, for example, a reporter molecule which is bound to facilitate its detection, and non-naturally occurring amino acid residues relative to the amino acid sequence of a naturally-occurring protein.

"Active fragments" encompasses at least five contiguous amino acid residues of a protein, which residues retain similar biological and/or functional activity to the naturally occurring protein.

The methods according to the invention may also be practised using nucleic acid sequences capable of hybridizing with cell cycle control genes (which hybridizing sequences encode cell cycle control proteins). The term "hybridization" as defined herein is a process wherein substantially homologous complementary nucleotide sequences anneal to each other. The hybridization process can occur entirely in solution, i.e. both complementary nucleic acids are in solution. Tools in molecular biology relying on such a process include the polymerase chain reaction (PCR; and all methods based thereon), subtractive hybridization, random primer extension, nuclease S1 mapping, primer extension, reverse transcription, cDNA synthesis, differential display of RNAs, and DNA sequence determination. The hybridization process can also occur with one of the complementary nucleic acids immobilised to a matrix such as magnetic beads, Sepharose beads or any other resin. Tools in molecular biology relying on such a process include the isolation of poly (A$^+$) mRNA. The hybridisation process can furthermore occur with one of the complementary nucleic acids immobilised to a solid support such as a nitro-cellulose or nylon membrane or immobilised by e.g. photolithography to, for example, a siliceous glass support (the latter known as nucleic acid arrays or microarrays or as nucleic acid chips). Tools in molecular biology relying on such a process include RNA and DNA gel blot analysis, colony hybridisation, plaque hybridisation, in situ hybridisation and microarray hybridisation. In order to allow hybridisation to occur, the nucleic acid molecules are generally thermally or chemically denatured to melt a double strand into two single strands and/or to remove hairpins or other secondary structures from single stranded nucleic acids. The stringency of hybridisation is influenced by conditions such as temperature, salt concentration and hybridisation buffer composition. High stringency conditions for hybridisation include high temperature and/or low salt concentration (salts include NaCl and Na$_3$-citrate) and/or the inclusion of formamide in the hybridisation buffer and/or lowering the concentration of compounds such as SDS (sodium dodecyl sulphate detergent) in the hybridisation buffer and/or exclusion of compounds such as dextran sulphate or polyethylene glycol (promoting molecular crowding) from the hybridisation buffer. Conventional hybridisation conditions are described in, for example, Sambrook (2001) Molecular Cloning: a laboratory manual, 3rd Edition Cold Spring Harbor Laboratory Press, CSH, New York, but the skilled artisan will appreciate that numerous different hybridisation conditions can be designed in function of the known or the expected homology and/or length of the nucleic acid sequence. Specifically hybridising refers to hybridising under stringent conditions, i.e. at a temperature of 60° C. followed by washes in 2×SSC (standard saline citrate), 0.1×SDS, and 1×SSC, 0.1× SDS. Sufficiently low stringency hybridisation conditions are particularly preferred for the isolation of nucleic acids homologous to the DNA sequences of the invention defined supra. Elements contributing to homology include allelism, degeneration of the genetic code and differences in preferred codon usage.

The methods according to the present invention may also be practised using an alternative splice variant of a cell cycle control gene. The term "alternative splice variant" as used herein encompasses variants of a nucleic acid sequence in which selected introns and/or exons have been excised, replaced or added. Such variants will be ones in which the biological activity of the protein remains unaffected, which can be achieved by selectively retaining functional segments of the protein. Such splice variants may be found in nature or can be manmade. Methods for making such splice variants are well known in the art. Preferably, the splice variant is a splice variant of the sequence represented by any of SEQ ID NO: 1, SEQ ID NO: 3 or SEQ ID NO: 5.

Advantageously, the methods according to the present invention may also be practised using allelic variants of a cell cycle control gene, preferably an allelic variant of a sequence represented by any of SEQ ID NO: 1, SEQ ID NO: 3 or SEQ ID NO: 5. Allelic variants exist in nature and encompassed within the methods of the present invention is the use of these natural alleles.

The methods according to the present invention may also be practised by introducing into a plant cell at least a part of a (natural or artificial) chromosome (such as a Bacterial Artificial Chromosome (BAC)), which chromosome contains at least a gene/nucleic acid sequence encoding a cell cycle control gene (such as SEQ ID NO: 1, SEQ ID NO: 3 or SEQ ID NO: 5), preferably together with one or more related gene family members.

The so manufactured expression construct may be transformed in plants so that the construct is stably integrated into the plant genome. The invention therefore provides genetic constructs and vectors to facilitate introduction and/or expression of the nucleotide sequences useful in the methods hereinbefore described. The present invention therefore provides a gene construct comprising: an epidermis-preferred promoter operably linked to a cell cycle control gene. Preferably, the 3' end of the cell cycle control gene is operably linked to a transcription termination sequence.

Constructs useful in the methods according to the present invention may be constructed using recombinant DNA technology well known to persons skilled in the art. The gene constructs may be inserted into vectors, which may be commercially available, suitable for transforming into plants and suitable for expression of the gene of interest in the transformed cells. Preferred cell cycle control genes are as represented by SEQ ID NO: 1, SEQ ID NO: 3 or SEQ ID NO: 5 or a portion of any of the aforementioned or sequences capable of hybridising with any of the aforementioned sequences or a nucleic acid sequence encoding a sequence represented by SEQ ID NO: 2, SEQ ID NO: 4 or SEQ ID NO: 6 or a homologue, derivative or active fragment thereof. Promoters suitable for practising the methods according to the invention are as hereinbefore described.

Optionally, one or more terminator sequences may also be used in the construct introduced into the plant. The term "terminator" encompasses a control sequence which is a DNA sequence at the end of a transcriptional unit which signals 3' processing and polyadenylation of a primary transcript and termination of transcription. Additional regulatory elements may include transcriptional as well as translational enhancers. Those skilled in the art will be aware of terminator and enhancer sequences suitable for use in performing the invention. Such sequences would be known or may readily be obtained by a person skilled in the art.

The genetic constructs of the invention may further include an origin of replication sequence which is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the fl-ori and colE1.

The genetic construct may optionally comprise a selectable marker gene. As used herein, the term "selectable marker gene" includes any gene which confers a phenotype on a cell in which it is expressed to facilitate the identification and/or selection of cells which are transfected or transformed with a nucleic acid construct of the invention. Suitable markers may be selected from markers that confer antibiotic or herbicide resistance. Cells containing the recombinant DNA will thus be able to survive in the presence of antibiotic or herbicide concentrations that kill untransformed cells. Examples of selectable marker genes include the bar gene which provides resistance to the herbicide Basta; the npt gene which confers resistance to the antibiotic kanamycin; the hpt gene which confers hygromycin resistance. Visual markers, such as the Green Fluorescent Protein (GFP, Haseloff et al., 1997), β-glucuronidase (GUS) or luciferase may also be used as selectable markers. Further examples of suitable selectable marker genes include the ampicillin resistance ($Amp^R$), tetracycline resistance gene ($Tc^R$), bacterial kanamycin resistance gene ($Kan^R$), phosphinothricin resistance gene, neomycin phosphotransferase gene (nptII), hygromycin resistance gene, and the chloramphenicol acetyltransferase (CAT) gene, amongst others.

The present invention encompasses enhanced or increased expression of a nucleic acid encoding a cell cycle control protein. Methods for obtaining enhanced or increased expression of genes or gene products are well documented in the art and include, for example, overexpression driven by a strong promoter, the use of transcription enhancers or translation enhancers.

According to another aspect of the present invention, decreased expression of a nucleic acid sequence encoding a cell cycle control protein is envisaged. Modulating gene expression encompasses altered transcript levels of a gene. Altered transcript levels can be sufficient to induce certain phenotypic effects, for example via the mechanism of cosuppression. In cosuppression, the overall effect of overexpression of a transgene is that there is less activity in the cell of the protein encoded by a native gene having homology to the introduced transgene. Other examples of decreasing expression are also well documented in the art and include, for example, downregulation of expression by anti-sense techniques, co-suppression techniques, RNAi techniques, small interference RNAs (siRNAs), microRNA (miRNA), the use of ribozymes, etc. Advantageously, the methods according to the present invention may also be practised by downregulation of a nucleic acid sequence encoding a cell cycle control protein. Techniques for downregulation are well known in the art. The terms "gene silencing" or "downregulation" of expression, as used herein, refer to lowering levels of gene expression and/or levels of active gene product and/or levels of gene product activity. Such decreases in expression may be accomplished by, for example, the addition of coding sequences or parts thereof in a sense orientation (if it is desired to achieve co-suppression). Therefore, according to one aspect of the present invention, the gene silencing may be achieved by introducing into a plant cell an additional copy (in full or in part) of a cell cycle control gene already present in a host plant. The additional gene will silence the endogenous gene, giving rise to a phenomenon known as co-suppression.

Genetic constructs aimed at silencing gene expression may comprise the cell cycle control gene, for example as represented by any of SEQ ID NO: 1, SEQ ID NO: 3 or SEQ ID NO: 5 (or one or more portions of any of the aforementioned sequences) in a sense and/or antisense orientation relative to the promoter sequence. The sense or antisense copies of at least part of the endogenous gene in the form of direct or inverted repeats may be utilised in the methods according to the invention. It should be clear that part of the nucleic acid (a portion) could achieve the desired result. Homologous antisense genes are preferred to heterologous anti-sense genes, homologous genes being plant genes, preferably plant genes from the same plant species, and heterologous genes being genes from non-plant species.

Another method for downregulation of gene expression or gene silencing comprises use of ribozymes, for example as described in Atkins et al. 1994 (WO 94/00012), Lenee et al. 1995 (WO 95/03404), Lutziger et al. 2000 (WO 00/00619), Prinsen et al. 1997 (WO 97/3865) and Scott et al. 1997 (WO 97/38116), the disclosures of which are incorporated by reference herein as if fully set forth.

Gene silencing may also be achieved by insertion mutagenesis (for example, T-DNA insertion or transposon insertion) or by gene silencing strategies as described by, among others, Angell and Baulcombe 1998 (WO 98/36083), Lowe et al. 1989 (WO 98/53083), Lederer et al. 1999 (WO 99/15682) or Wang et al. 1999 (WO 99/53050), which are incorporated by reference herein as if fully set forth. Expression of an endogenous gene may also be reduced if the endogenous gene contains a mutation. Such a mutant gene may be isolated and introduced into the same or different plant species in order to obtain plants having modified epidermal outgrowth structures.

As used herein, the term 'plant' includes reference to whole plants, plant organs (such as leaves, roots, stems, etc.), seeds and plant cells and ancestors and progeny of same. 'Plant cell', as used herein includes protoplasts, suspension cultures, embryos, meristematic regions, callus tissue, leaves, seeds, roots, shoots, gametophytes, sporophytes, pollen, and microspores. Plants that can be used in the methods of the invention include all plants which belong to the superfamily Viridiplantae, including both monocotyledonous and dicotyledonous plants, including fodder or forage legumes, ornamental plants, food crops, trees, or shrubs selected from the list comprising *Acacia* spp., *Acer* spp., *Actinidia* spp., *Aesculis* spp., *Agathis australi, Albizia amara, Alsophila tricolor, Andropogon* spp., *Arachis* spp, *Areca catechu, Astelia fragrans, Astragalus cicer, Baikiaea plurijuga, Betula* spp., *Brassica* spp., *Bruguiera gymnorrhiza, Burkea africana, Butea frondosa, Cadaba farinosa, Calliandra* spp, *Camellia sinensis, Canna indica, Capsicum* spp., *Cassia* spp., *Centroema pubescens, Chaenonieles* spp., *Cinnamonum cassia,*

Coffea arabica, Colophospermum mopane, Coronillia varia, Cotoneaster serotina, Crataegus spp., Cucumis spp., Cupressus spp., Cyathea dealbata, Cydonia oblonga, Cryptomeria japonica, Cymbopogon spp., Cynthea dealbata, Cydonia oblonga, Dalbergia monetaria, Davallia divaricata, Desmodium spp., Dicksonia squarosa, Diheteropogon amplectens, Dioclea spp, Dolichos spp., Dorycnium rectum, Echinochloa pyramidalis, Ehrartia spp., Eleusine coracana, Eragrestis spp., Eryhrina spp., Eucalyptus spp., Euclea schimperi, Eulalia villosa, Fagopyrum spp., Feijoa sellowiana, Fragaria spp., Flemingia spp, Freycinetia banksii, Geraniumn thunbergii, Ginkgo biloba, Glycine javanica, Gliricidia spp, Gossypium hirsutum, Grevillea spp., Guibourtia coleosperma, Hedysarum spp., Hemarthia altissima, Heteropogon contortus, Hordeum vulgare, Hyparrhenia rufa, Hypericum erectum, Hyperthelia dissoluta, Indigo incarnata, Iris spp., Leptarrhena pyrolifolia, Lespediza spp., Lettuca spp., Leucaena leucocephala, Loudetia simplex, Lotonus bainesii, Lotus spp., Macrotyloma axillare, Malus spp., Manihot esculenta, Medicago sativa, Metasequoia glyptostroboides, Musa sapientum, Nicotianum spp., Onobrychis spp., Ornithopus spp., Oryza spp., Peltophorum africanum, Pennisetum spp., Persea gratissima, Petunia spp., Phaseolus spp., Phoenix canariensis, Phormium cookianum, Photinia spp., Picea glauca, Pinus spp., Pisum sativum, Podocarpus totara, Pogonarthria fleckii, Pogonarthria squarrosa, Populus spp., Prosopis cineraria, Pseudotsuga menziesii, Pterolobium stellatum, Pyrus communis, Quercus spp., Rhaphiolepsis umbellata, Rhopalostylis sapida, Rhus natalensis, Ribes grossularia, Ribes spp., Robinia pseudoacacia, Rosa spp., Rubus spp., Salix spp., Schyzachyrium sanguineum, Sciadopitys verticillata, Sequoia sempervirens, Sequoiadendron giganteum, Sorghum bicolor, Spinacia spp., Sporobolus fimbriatus, Stiburus alopecuroides, Stylosanthos humilis, Tadehagi spp, Taxodium distichum, Themeda triandra, Trifolium spp., Triticum spp., Tsuga heterophylla, Vaccinium spp., Vicia spp., Vitis vinifera, Watsonia pyramidata, Zantedeschia aethiopica, Zea mays, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, trees and algae amongst others. Particularly preferred plants are those having plant epidermal outgrowth structures such as aerial (above ground) structures including but not limited to trichomes (plant hair), as well as subterrestrial structures such as root hairs. However, any plant species, (either monocot or dicot and including crop plants and ornamentals, herbaceous or woody), may be used in and can be benefited by, compositions and methods of the present invention.

The cell cycle control protein itself and/or the cell cycle control gene itself may be introduced directly into a plant cell. According to a preferred feature of the present invention, the cell cycle control gene is transformed into a plant. The term "transformation" as referred to herein encompasses the transfer of an exogenous polynucleotide into a host cell, irrespective of the method used for transfer. In accordance with the present invention, any plant species may be transformed with a subject expression construct. Thus, transformation procedure might differ among plant species and may be adjusted accordingly. For example, a subject expression construct may be introduced into a plant or plant cell via any of the well known methods of gene transfer in plants. Methods of gene transfer in plants are well known (see e.g., Gelvin 1998 Current Opin. Biotech. 9:227) and include, for example, transformation of plant cells or tissues with T-DNA using Agrobacterium tumefaciens or Agrobacterium rhizogenes as described essentially by An et al. (EMBO J 4:277-284, 1985), Herrera-Estrella et al (Nature 303: 209-213, 1983a; EMBO J. 2:987-995, 1983b), Bechtold et al., (C.R. Acad. Sci. (Paris 316: 1194-1199, 1993) or Clough et al (Plant J. 16: 735-743, 1998); protoplast fusion, micoinjection (Potrykus and Spangenberg (eds.), Gene Transfer To Plants. Springer Verlag, Berlin, N.Y. 1995); electroporation (Fromm e al., Proc. Natl. Acad. Sci. USA 82:5824-5828, 1985); biolistic methods like particle bombardment (Wan, Plant Physiol. 104 (1994), 37-48; Vasil, Bio/Technology 11 (1993), 1553-1558 and Christou (1996) Trends in Plant Science 1, 423-431), pollen-mediated transformation, plant virus-mediated transformation, liposome-mediated transformation, transformation using wounded or enzyme-degraded immature embryos, or wounded or enzyme-degraded embryogenic callus and other methods known in the art.

For Arabidopsis the standard procedure is an Agrobacterium mediated transfer of DNA fragments (Koncz and Schell, 1986; Clough and Bent, 1998). Identification of transgenic plants can be achieved by cotransforming a gene which mediates resistance against a herbicide. Alternatively other markers can be used, e.g. visual markers, which allow an identification of a successful gene transfer. Selectable marker genes useful for the selection of transformed plant cells, callus, plant tissue and plants are well known to those skilled in the art. For example, antimetabolite resistance provides the basis of selection for: the dhfr gene, which confers resistance to methotrexate (Reiss, Plant Physiol. (Life Sci. Adv.) 13 (1994), 143-149); the npt gene, which confers resistance to the aminoglycosides neomycin, kanamycin and paromomycin (Herrera-Estrella, EMBO J. 2 (1983), 987-995); and hpt, which confers resistance to hygromycin (Marsh, Gene 32 (1984), 481-485). Useful scorable markers are also known to those skilled in the art and are commercially available. For example, the genes encoding luciferase (Giacomin, Pl. Sci. 116 (1996), 59-72; Scikantha, J. Bact. 178 (1996), 121), green fluorescent protein (Gerdes, FEBS Lett. 389 (1996), 44-47) or β-glucuronidase (Jefferson, EMBO J. 6 (1987), 3901-3907) may be used.

Generally after transformation, plant cells or cell groupings are selected for the presence of one or more markers which are encoded by plant-expressible genes co-transferred with the gene of interest, following which the transformed material is regenerated into a whole plant.

Following DNA transfer and regeneration, putatively transformed plants may be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed to give homozygous second generation (or T2) transformants, and the T2 plants further propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced in the parent by the methods according to the invention.

The invention also includes host cells containing a cell cycle control gene under the control of an epidermal structure-preferred promoter. Preferred host cells according to the invention are plant cells. The invention also extends to harvestable parts of a plant such as but not limited to seeds, leaves, fruits, flowers, stem cultures, rhizomes, tubers and bulbs, which harvestable parts comprise modified epidermal outgrowth structures.

The present invention also encompasses plants obtainable by the methods according to the present invention, which plants have modified epidermal outgrowth structures. The present invention therefore provides plants obtainable by the method according to the present invention, which plants have modified epidermal outgrowth structures and which plants have altered expression of a nucleic acid sequence encoding a cell cycle control protein.

According to another embodiment of the present invention, there is provided a method for the production of transgenic plants having modified epidermal outgrowth structures, comprising introduction and expression in a plant of a cell cycle control protein.

More specifically, the present invention provides a method for the production of transgenic plants having modified epidermal outgrowth structures, which method comprises:

(i) introducing into a plant or plant cell a nucleic acid sequence or a portion thereof encoding a cell cycle control protein or a homologue, derivative or active fragment thereof, which cell cycle control protein is operably linked to an epidermal structure-preferred promoter;

(ii) cultivating the plant cell under conditions promoting regeneration and mature plant growth.

Examples of modified epidermal growth structures include aerial (above ground) structures such as trichomes (plant hairs). Epidermal outgrowth structures also include but are not limited to subterrestrial structures such as root hairs.

Epidermal growth structures may be further modified by combining expression of a cell cycle gene (under the control of a first epidermis-preferred promoter) with expression of a growth enhancement gene (under the control of a second epidermis-preferred promoter). The reason for a first and second epidermis-preferred promoter is so as to avoid inadvertent silencing that might take place if two substantially similar promoters are used. The expression of the growth enhancement gene (such as any hormone metabolism enzyme, any gene encoding a cell wall component, any elongation factor, cytoskeleton genes) will lead to enhanced growth of the trichome, resulting in bigger trichomes and/or a greater number of trichomes. The expression of the cell cycle gene in trichome structures will also lead to modified trichome structures as hereinbefore described. This dual expression has various economic advantages, for instance, where it is wished to exploit the trichome structure for the manufacture of useful substances (see for instance Examples 4). The bigger the size of the trichome or the greater the trichome number, the greater the resultant product of interest.

In accordance with the present invention, there are provided transgenic plants which ectopically express a cell cycle control protein in an epidermal outgrowth structure. Such transgenic plants have modified morphological, biochemical, or physiological properties or characteristics in the epidermal outgrowth structure such as a trichome or root hair. Examples of such modifications include increased cell division, increased nuclear division, and increased DNA replication.

The present invention also provides a method for making a plant having a modified epidermal outgrowth structure. The method comprises the steps of transforming a plant cell with a cell cycle control gene operably linked to an epidermis-preferred promoter and regenerating a plant from the transformed plant cell, wherein the regenerated plant has a modified epidermal outgrowth structure. Plants having a modified epidermal outgrowth structure produced by the above-described method are also provided.

Products produced in plant trichomes or root hairs may be manipulated in various ways. Thus for example, by reducing expression of KRP transcript levels in epidermal outgrowth structures, trichomes exhibit an increase in endoreduplication and thus an increase in cell size and products produced in the cells. Such products may be isolated by harvesting the plant and removing the trichomes or root hairs from the plant. Trichome and root hair removal can be achieved by freezing the plant, in which case the structures drop off from the plant. Mechanical means such as gentle rubbing may also be used to remove trichomes or root hairs. The product produced in the root hair or trichome may then be extracted using well known methods. Purification of the product produced in the trichome or root hair may also be performed using well known methods.

A method for identifying cell cycle control genes capable of modifying the morphological, biochemical, physiological properties or characteristics of a plant epidermal outgrowth structure is also provided. The method comprises the steps of: transforming a plant with a cell cycle control gene operably linked to an epidermis-preferred promoter; monitoring changes in the morphological, biochemical, physiological properties or characteristics of plant epidermal outgrowth structure of said transformed plant relative to corresponding wild-type plants; and identifying cell cycle genes capable of modifying morphological, biochemical, physiological properties or characteristics of plant epidermal outgrowth structures.

The following examples further illustrate the invention.

DNA Manipulation

Unless otherwise stated, recombinant DNA techniques are performed according to standard protocols described in (Sambrook (2001) Molecular Cloning: A Laboratory Manual, 3rd Edition, Cold Spring Harbor Laboratory Press, CSH, New York) or in Ausubel et al. (1994), Current Protocols in Molecular Biology (Wiley, New York). Standard materials and methods for plant molecular work are described in Plant Molecular Biology Labfase (1993) by R. D. D. Croy, published by BIOS Scientific Publications Ltd (UK) and Blackwell Scientific Publications (UK).

EXAMPLE 1

Expression of CYCLIN B1;2 in Leaf Hairs of *Arabidopsis*

Wild-type *Arabidopsis* plants do not express CYCLIN B1;2 in trichomes as judged by the analysis of the promoter activity of the CYCLIN B1;2 gene or the detection of the CYCLIN B1;2 RNA.

Cell Control Constructs

To generate the PGL2::CYCB1;2 construct, CYCB1;2 cDNA (cyc1bAt) was excised from pBS SK CYCB1;2 (Day et al., 1996) with BamHI and Acc65, treated with Klenow fragment, and inserted into the BamHI and Ecl136Il sites of pBl101.1pGL2 to yield plasmid pART60. To achieve trichome expression, a 2.1-kb HindIII/NheI fragment from the 5' upstream region of the GLA-BRA2 gene (Szymanski et al., 1998) was used. To generate the pCYCB1;2::GUS construct (pART51); 1059 bp of the genomic region 5' of the CYCB1;2 gene (amplified from Columbia genomic DNA with the primers 5'-ACCTGCAGGTGTAAGTTTTGATCACATC-CTCTTG-3' (SEQ ID NO:8), containing a Sse8387I site, and 5'-AGTCGACATCGCTCTCCCAATGATTCTTAC-3' (SEQ ID NO:9), including a SalI site) were cloned 5' of a GUS reporter gene fused to the destruction box of CYCB1;1 (pCD-BGUS2); 3' to the DBGUS, a 809-bp fragment from the 3' region of the CYCB1;2 gene was inserted (amplified from Columbia genomic DNA with the primers 5'-AGAGCTCT-GAATGGAAGAAGCCTGTTTC-3' (SEQ ID NO: 10), containing a SacI site, and 5'-ACCCGGGACGAGAATCAAC-CCCGTGAG-3' (SEQ ID NO:11), including a SmaI site.

To generate plants which express the CYCLIN B1;2 cDNA in trichomes (pGL2::CYCB1;2) the CYCB1;2 cDNA was excised from pBS SK CYCB1;2 (Day et al., 1996) and inserted in pBI101.1pGL2 (Szymanski et al., 1998). The pB101.1pGL2 plasmid contains a 2.1 kb HindIII/NheI fragment from the 5'-upstream region of the GLABRA2 gene to achieve expression with in trichomes.

Plant Material, Growth Conditions and Plant Transformation

The *Arabidopsis* ecotype Landsberg erecta (Ler) was used as a wild-type control. The plasmid was introduced into *Agrobacterium* strain GV3101(pMP90) (Koncz and Schell, 1986) by electroporation and transformed into Ler by the floral dip method (Clough and Bent, 1998). Transgenic plants were selected on MS plates (Murashige and Skoog, 1962) containing 3% sucrose with Kanamycin at 50 μg per ml. The presence of the transgene was verified by PCR and RT PCR.

Multicellular trichomes arising from CYCB1;2 expression did not surmount the regular wild-type DNA content of 32C, which indicates that CYCB1;2 acts downstream of factors controlling the number of cell-cycle rounds. SEQ ID NO: 3 depicts the CYCB1;2 nucleic acid sequence. Transgenic lines expressing CYCB1;2 in trichomes displayed altered trichome characteristics relative to corresponding wild-type plants. For example, the cluster frequency was increased in comparison to wild-type, with up to 33% of all TIS having more than one trichome (FIGS. 7A, 7B and 7F and Table 3). Confocal laser microscopy showed more than one nucleus and several cell walls within one trichome (FIG. 7H). Thus CYCB1;2 expression transformed the single-celled trichomes into multicellular hairs. This finding was confirmed by light microscopic analysis of semithick sections (FIG. 8F) and transmission electron microscopy of ultrathin sections (FIGS. 8A-8D).

GUS Assays

Whole-mount GUS stainings were performed as described in Schoof et al. (2000).

In Situ RNA Hybridization

An antisense probe from a full-length CYCB1;2 cDNA clone was generated using T7 RNA polymerase; a sense probe was synthesized using T3 RNA polymerase, and for both CYCB1;2 probes, the template was vector pBS SK CYCB1;2. An antisense probe for KN was synthesized with T7 RNA polymerase from plasmid pHB02-B10 digested with XhoI; a sense probe was synthesized using T3 RNA polymerase from plasmid pHB02-B10 digested with XbaI. PHB02-B10 contains a 200-bp fragment from 5' region of the K-coding region (Lukowitz, 1996).

RT-PCR Analysis

An RNA template was prepared with Dynabeeds (DYNAL) and was treated with DnaseI to remove genomic DNA contamination. RT-PCR was carried out with TITAN One tube RT-PCR mix (Roche Diagnostics) with a 5' primer in the 5' UTR of the GL2 gene included in the GL2 promoter fragment used and with a 3' primer of the respective cyclin or the GL2 gene. A total of 5 μl of the RT-PCR product after cycles 15, 18, 21, 24 and 27 were separated on an agarose gel, blotted onto a Hybond N+ membrane (Amersham), and hybridized with the respective cDNA probes labelled with DIG labelling mix (Roche Diagnostics).

Microscopy

Leaves from 2-week-old plants were cryofixed by dipping them into liquid nitrogen-cooled propane, followed by freeze substitution in anhydrous acetone containing 1% glutaraldehyde and 2% osmium tretoxide (−90° C.: 35 hr; −60° C.: 6 hr; 0° C.: 1 hr; in some cases, +20° C.: 1 hr). After washing them with pure ethanol, leaves were stained with 2% uranyl acetate in pure ethanol for 1 hr and embedded in Spuur's resin. For light microscopy, semithick (1 μm) sections were stained with Toluidine Blue; for electron microscopy ultrathin sections were stained with ethanolic uranyl acetate and lead citrate. For confocal laser scanning microscopy, whole-mount stainings with CYTO13 (Molecular Probes) were analyzed as described (Schnittger et al., 1998). Cryo-scanning electron microscopy was performed as described in Rumbolz (1999).

DNA Measurements

Trichome nuclei were measured as described in Schnittger et al. (1998).

Other Techniques

All sequencing work was done using the ABI PRISM Big-Dye Terminator cycle sequencing kit and the ABI sequencer 310 (Applied Biosystems). Alignments were done with the ClustalW and BLAST 2 sequences algorithm (Tatusova, T. A., and Madden, T. L., 1999; Thompson, J. D., et al., 1994). Images were processed with Adobe Photoshop 6.0 and Adobe Illustrator 9.0 software.

EXAMPLE 2

Expression of CYCLIN D3;1 in Leaf Hairs of *Arabidopsis*

Wild-type *Arabidopsis* plants do not express CYCLIN D3;1 in trichomes as judged by the analysis of the CYCLIN D3;1 RNA by in situ hybridization. To generate plants which express the CYCLIN D3;1 cDNA in trichomes pGL2::CYCD3;1) the CYCD3;1 cDNA was excised from pBSCYCD3;1 (Riou-Khamlichi et al., 1999) and inserted in pBI101.1pGL2 (Szymanski et al., 1998). The pB101.1pGL2 plasmid contains a 2.1 kb HindIII/NheI fragment from the 5'-upstream region of the GLABRA2 gene to achieve expression within trichomes.

The plasmid was introduced into *Agrobacterium* strain GV3101 (pMP90) (Koncz and Schell, 1986) by electroporation and transformed into Ler by the floral dip method (Clough and Bent, 1998). Transgenic plants were selected on MS plates (Murashige and Skoog, 1962) containing 3% sucrose with Kanamycin at 50 μg per ml. The presence of the transgene was verified by PCR and RT-PCR.

Figure 1:
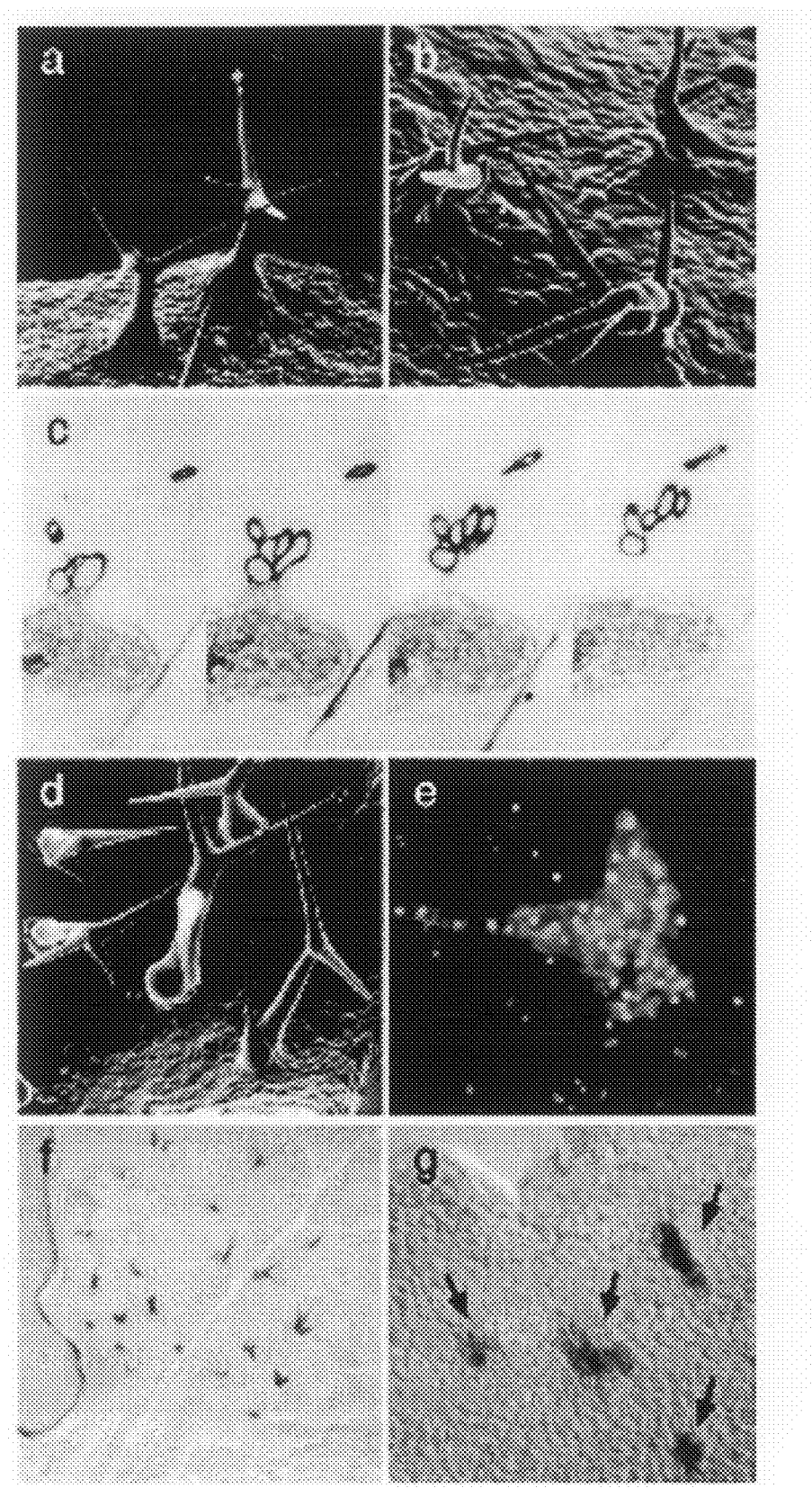
FIG. 1: Morphological analysis.

Mutant trichomes with a lesser DNA content (e.g., 16C) are smaller and have fewer branches, whereas trichomes with a higher DNA content (e.g., 64C) are larger and develop more branches. However, instead of larger cells with more branches, the ectopic expression of CYCD3;1 induced cell divisions that led to multicellular trichomes. This increasing number of cells resulted in an increase in the total DNA content. CYCD3;1 therefore, can influence the number of cell cycles. Scanning electron microscopy indicated multiple cells per trichome (FIGS. 1 a, b and d), which was confirmed by light microscopical analysis of consecutive sections (FIG. 1c). By confocal laser microscopy of CYTO13-stained leaves, multiple nuclei could be found in one trichome. Whereas trichomes on wild-type plants are spaced separately over the leaf blade (FIG. 1a), trichomes on pGL2::CYCD3;1 plants developed more than one trichome initiation site (TIS), resulting in clusters of trichomes (FIGS. 1 b and D; Table 2). These clusters were caused by cell divisions at very early stages of trichome development before trichome outgrowth (FIG. 2 a-d). Furthermore, a higher number of cells per TIS may be correlated with stronger expression of the transgene (FIG. 3; Table 2). Advantageously, cells within a multicellular trichome have a trichome fate, therefore the induction of cell divisions does not appear to interfere with cell differentiation (FIGS. 1f and g and FIG. 2 d). Expression of CYCD3;1 not only promoted S-phase entry but also induced mitosis.

Glucuronidase (GUS) Assays

Whole-mount GUS stainings were performed as described by Schoof et al. (2000).

Reverse Transcription (RT)-PCR Analysis

RNA template, prepared with Dynabeads (Dynal, Oslo), was treated with DNase I to remove genomic DNA contamination. RT-PCR was carried out with the TITAN One tube RT-PCR mix (Roche Diagnostics). The 5' primer used was designed against the 5' untranslated region of the GL2 gene included in the GL2 promoter fragment used in vector construction, and the 3' primer were designed against the respective cyclin or GL2 gene. After cycles 15, 18, 21, 24, and 27, 5 µl of the RT-PCR products were separated on an agarose gel, blotted onto a Hybond N$^+$ membrane (Amersham Pharmacia), and hybridized with the respective cDNA probes labeled with the digoxigenin-labeling mix (Roche Diagnostics).

Microscopy

Leaves from 2-week-old plants were cryofixed by dipping into liquid nitrogen-cooled propane followed by freeze substitution in anhydrous acetone containing 1% glutaraldehyde and 2% osmium tetroxide (–90° C., 35 h; –60° C., 6 h; –35° C., 6 h; 0° C., 1 h; in some cases 20° C., 1 h). After washing with pure ethanol, the leaves were stained with 2% uranyl acetate in pure ethanol for 1 h and embedded in Spurr's resin. Semithick (1-µm) sections were stained with toluidine blue and analyzed in the light microscope. For confocal laser scanning microscopy, whole-mount stainings with CYTO13 (Molecular Probes) were analyzed as described in Schnittger A., et al. 1998. Cryoscanning electron microscopy was performed as described by Rumbolz et al. (1999)

DNA Measurements

Trichome nuclei were measured as described by Schnittger et al. (1998).

Expression of CYCD3;1 Increases the Total DNA Content in Trichomes

To analyze whether CYCD3;1 expression converted the endoreduplication cycle into a mitotic cycle, the DNA content of pGL2::CYCD3;1 trichome nuclei in comparison to wild-type trichomes as well as two mutants with known alterations in ploidy level: glabra 3 (gl3) trichomes, was determined. These mutants show on average one round of endoreduplication less than wild type, resulting in 16C, and triptychon (try) with roughly one additional round, giving rise to a nuclear content of 64C (FIG. 4 a-c). It was found that expression of CYCD3;1 interfered with but did not totally abolish endoreduplication (FIG. 4 d-h). Overall, single nuclei in a multicellular trichome ranged from 4C to 20C (FIG. 4 e-h). There was a negative correlation between the number of cells per trichome initiation site (TIS) and their nuclear size; the more cells that were in a TIS the less their single-cell DNA content was. However, even in the strongly expressing line #1, a few nuclei with a DNA content of about 16C could be detected (FIG. 4h). Also by expressing CYCB1;2 in trichomes multicellular trichomes arise (Schnittger, A. et al. 2002). There, a similar correlation between an increasing number of cells per trichomes and a decreasing amount of DNA can be found. Summing up the DNA content of all single nuclei in pGL2::CYCB1;2 trichomes as being the total DNA content per TIS revealed that the wild-type total DNA content of 32C would not be exceeded. Therefore, the total DNA content per TIS in pGL2::CYCD3;1 plants was analyzed. As opposed to CYCB1;2 expression, the wild-type DNA content of 32C was surmounted by CYCD3;1 expression and appeared to rise with the number of cells per TIS from on average 40C in two nucleated trichomes in line 2 to more than 80C in multinucleated trichomes of line #1 (FIG. 4 e-h). Therefore CYCD3;1 expression also promoted entry into S phase.

EXAMPLE 3

Expression of KIP-RELATED-PROTEIN 1 in Leaf Hairs of *Arabidopsis*

The KRP family of cell cycle regulators comprises in *Arabidopsis* 7 members which share a conserved C-terminal region (De Veylder et al., 2001). To generate plants which express the KRP1 cDNA in trichomes cDNA was PCR amplified from a cDNA library and subcloned into pBS. Next the cDNA was excised from pBS and inserted in pBI101.1pGL2 (Szymanski et al., 1998). The pB101.1pGL2 plasmid contains a 2.1 kb HindIII/NheI fragment from the 5'-upstream region of the GLABRA2 gene to achieve expression with in trichomes.

The plasmid was introduced into *Agrobacterium* strain GV3101(pMP90) (Koncz and Schell, 1986) by electroporation and transformed into Ler by the floral dip method (Clough and Bent, 1998). Transgenic plants were selected on MS plates (Murashige and Skoog, 1962) containing 3% sucrose with Kanamycin at 50 µg per ml. The presence of the transgene was verified by PCR.

Phenotypic analysis (by light microscope, laser scanning confocal microscope, and other techniques) shows that expression of the KRP1 results in plant hairs with a reduced cell size and reduced endoreduplication level in comparison with wild-type *Arabidopsis* trichomes (FIG. 10 and FIG. 11).

EXAMPLE 4

Expression of CYCLIN D3;1 in Cotton Trichomes

The cotton fiber specific LTP3 promoter (Liu et al., 2000) is cloned in front of the *Arabidopsis* CYCLIN D3;1 cDNA (Riou-Khamlichi et al., 1999) to express CYCLIN D3;1 in cotton trichomes (cotton fibers). After transformation of this construct into cotton plants the cotton trichomes are formed in clusters. This leads to a more densely haired ovule and thus to an increased cotton production per plant.

EXAMPLE 5

Down Regulation of KRP Function in Peppermint Trichomes

Gene activity may be reduced in accordance with the present invention by a reduction of KRP transcript levels using a gene silencing mechanism based on the generation of double stranded RNA pieces of the respective gene. An RNAi (RNA interference) construct against this conserved region is expressed in peppermint trichomes silencing KRP function there. The silencing results in an increased endoreduplication level in peppermint trichomes and leads thus to an increase in cell size. In this way enlarged peppermint trichomes produce more oils.

EXAMPLE 6

Expression of CYCLIN D3;1 in Root Hairs of Plants Overexpressing Ferric-Chelate Reductase Low availability of iron often limits plant growth, therefore plants are genetically engineered for a ferric-chelate reductase to have an increased iron uptake (Robinson et al., 1999). The expression of the *Arabidopsis* cDNA for CYCLIN D3;1 (Riou-Khamlichi et al., 1999) in root hair cells of these already genetically modified plants increases the size of the root hairs leading to an increased surface and thus to an increased uptake of iron. This leads to a better plant growth and to an enrichment of iron in the food chain.

REFERENCES

Ausubel, F. M. (1994). Current protocols in molecular biology. (New York: John Wiley & Sons, Inc.).

Clough, S. J., and Bent, A. F. (1998). Floral dip: a simplified method for Agrobacterium-mediated transformation of *Arabidopsis thaliana*. Plant J 16, 735-743.

Cockcroft, C. E., den Boer, B. G., Healy, J. M., and Murray, J. A. (2000). Cyclin D control of growth rate in plants. Nature 405, 575-579.

Day, I. S., Reddy, A. S., and Golovkin, M. (1996). Isolation of a new mitotic-like cyclin from *Arabidopsis*: complementation of a yeast cyclin mutant with a plant cyclin. Plant Mol Biol 30, 565-575.

De Veylder, L., Beeckman, T., Beemster, G. T., Krols, L., Terras, F., Landrieu, I., van der Schueren, E., Maes, S., Naudts, M., and Inze, D. (2001). Functional analysis of cyclin-dependent kinase inhibitors of *Arabidopsis*. Plant Cell 13, 1653-1668.

Koncz, C., and Schell, J. (1986). The promoter of $T_L$-DNA gene 5 controls the tissue-specific expression of chimaeric genes carried by a novel *Agrobacterium* binary vector. Mol Gen Genet. 204, 383-396.

Liu, H. C., Creech, R. G., Jenkins, J. N., and Ma, D. P. (2000). Cloning and promoter analysis of the cotton lipid transfer protein gene Ltp3(1). Biochim Blophys Acta 1487, 106-111.

Lukowitz, W., Mayer, V., and Jurgens, G. (1996) Cytokinesis in the *Arabidopsis* embryo involves the syntaxin-related KNOLLE gene product. Cell, 84, 61-71.

Mandaci, S., and Dobres, M. S. (1997). A promoter directing epidermal expression in transgenic alfalfa. Plant Mol Biol 34, 961-965.

Murashige, T., and Skoog, F. (1962). A revised medium for rapid growth and bioassays with tobacco tissue cultures. Physiologia plantarum 15, 473-497.

Riou-Khamlichi, C., Huntley, R., Jacqmard, A., and Murray, J. A. (1999). Cytokinin activation of *Arabidopsis* cell division through a D-type cyclin. Science 283, 1541-1544.

Robinson, N. J., Procter, C. M., Connolly, E. L., and Guerinot, M. L. (1999). A ferric-chelate reductase for iron uptake from soils. Nature 397, 694-697.

Rumbolz, J, Kassemeyer, H. H., Steinmetz, V., Deising, H. B., Mendgen, K., Mathys, D., Wirtz, S., and Guggenhein, R. (1999). Differentiation of infection structures of powdery mildew fungus Uncinula necator and adhesion to the host cuticle. Can. J. Bot. 78, 409-421.

Sambrook, J., Fritsch, E., and Maniatis, T. (1989). Molecular cloning: a laboratory manual. (Cold Spring Harbor, N.Y.: Cold Spring Harbor Laboratory Press).

Schoof, H., Lehnard, M., Haecker, A., Mayer, K. F., Jurgens, G, Laux, T. (2000) Cell 100, 635-644.

Schnittger, A., Jurgens, G., and Hulskamp, M. (1998) Tissue layer and organ specificity of trimchome formation are regulated by GLABRA1 and TRIPTYCHON in *Arabidopsis*. Development 125, 2283-2289.

Szymanski, D. B., Jilk, R. A., Pollock, S. M., and Marks, M. D. (1998). Control of GL2 expression in *Arabidopsis* leaves and trichomes. Development 125, 1161-1171.

Tatusova, T. A., and Madden, T. L. (1999). BLAST 2 Sequences, a new tool for comparing protein and nucleotide sequences, FEMS Microbiol. Lett. 174, 247-250.

Thompson, J. D., Higgins, D. G. and Gibson, T. J. (1994) CLUSTAL W: improving the sensitivity of progressive multiple sequence alignment through sequence weighting, position-specific gap penalties and weight matrix choices. Nucleic Acids Res. 22, 4673-4680.

What is claimed is:

1. A method for producing a plant having a modified epidermal outgrowth structure, said method comprising: transforming a plant or plant cell with a cell cycle control gene operably linked to an epidermis-preferred promoter and regenerating a plant from the transformed plant or plant cell, wherein the regenerated plant has a modified epidermal outgrowth structure and wherein the cell cycle control gene encodes D-type cyclin CYCD3;1 having the sequence of SEQ ID NO:2.

2. The method of claim 1 wherein the epidermal outgrowth structure is above ground.

3. The method of claim 1 wherein the epidermal outgrowth structure is below ground.

4. The method of claim 2 wherein the epidermal outgrowth structure is a trichome.

5. The method of claim 3 wherein the epidermal outgrowth structure is a root hair.

6. The method of claim 1 wherein the epidermis-preferred promoter is selected from the group consisting of: a lipid transfer protein 3 gene promoter from cotton, a GLABRA2 gene promoter from *Arabidopsis*, a GORK gene promoter from *Arabidopsis*, a MIP-MOD gene promoter from *Brassica*, a BLEC4 gene promoter from *Pisum sativa*, a WAXD9 gene promoter from broccoli, and a MtENOD12 gene promoter from *Medicago trunculata*.

7. A plant having a modified epidermal outgrowth structure produced by the method of claim 1.

8. The method of claim 6 wherein the GLABRA2 gene is GL2.

9. The method of claim 6 wherein the lipid transfer protein 3 gene is LTP3.

* * * * *